(12) United States Patent
Gregg et al.

(10) Patent No.: US 11,707,366 B2
(45) Date of Patent: Jul. 25, 2023

(54) POWERED PROSTHESIS WITH TORQUE DENSE, LOW RATIO ACTUATION

(71) Applicant: Board of Regents, The University of Texas System, Austin, TX (US)

(72) Inventors: Robert D. Gregg, Richardson, TX (US); Toby B. Elery, Farmers Branch, TX (US); Christopher R. Nesler, Austin, TX (US); Siavash Rezazadeh, Addison, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/398,895

(22) Filed: Apr. 30, 2019

(65) Prior Publication Data
US 2019/0328551 A1 Oct. 31, 2019

Related U.S. Application Data

(60) Provisional application No. 62/664,655, filed on Apr. 30, 2018.

(51) Int. Cl.
*A61F 2/70* (2006.01)
*A61F 2/60* (2006.01)
*A61F 2/76* (2006.01)
*A61F 2/68* (2006.01)

(52) U.S. Cl.
CPC .................. *A61F 2/70* (2013.01); *A61F 2/60* (2013.01); *A61F 2/76* (2013.01);
(Continued)

(58) Field of Classification Search
CPC ...... A61F 2/70; A61F 2/60; A61F 2/76; A61F 2/604; A61F 2/605; A61F 2/64;
(Continued)

(56) References Cited

U.S. PATENT DOCUMENTS

| | | | | |
|---|---|---|---|---|
| 5,888,213 A * | 3/1999 | Sears | ........................ | A61F 2/68 623/24 |
| 2012/0259429 A1 * | 10/2012 | Han | ...................... | A61F 5/0127 623/24 |

(Continued)

OTHER PUBLICATIONS

Elery, T., et al., "Design and Validation of a Powered Knee-Ankle Prosthesis with High-Torque, Low-Impedance Actuators," IEEE Transactions on Robotics, vol. 36, No. 6, Dec. 2020, pp. 1649-1668.
(Continued)

*Primary Examiner* — Jerrah Edwards
*Assistant Examiner* — Aren Patel
(74) *Attorney, Agent, or Firm* — Parker Justiss, P.C.

(57) ABSTRACT

Disclosed herein are embodiments of a powered prosthesis. In one embodiment, the powered prosthesis may include a first joint actuator; a second joint actuator; a connector to connect the first joint actuator with the second joint actuator; and a power source connected with both the first and second joint actuator; wherein the first joint actuator and the second joint actuator are both at least backdrivable and configured such that when one of the first or second joint actuator is drawing power from the power source, the other of the first or second joint actuator may be generating power for the power source. In some embodiments, the first motor is at least a high output torque motor. In other embodiments, the second motor is at least a high output torque motor.

20 Claims, 22 Drawing Sheets

(52) U.S. Cl.
CPC . *A61F 2002/607* (2013.01); *A61F 2002/6836* (2013.01); *A61F 2002/701* (2013.01); *A61F 2002/764* (2013.01); *A61F 2002/768* (2013.01); *A61F 2002/7645* (2013.01)

(58) Field of Classification Search
CPC .................. A61F 2/68; A61F 2002/607; A61F 2002/6836; A61F 2002/701; A61F 2002/764; A61F 2002/7645; A61F 2002/768; A61F 2002/6607
See application file for complete search history.

(56) References Cited

U.S. PATENT DOCUMENTS

| | | | | |
|---|---|---|---|---|
| 2013/0261766 | A1* | 10/2013 | Langlois | A61F 2/605 623/33 |
| 2014/0142475 | A1* | 5/2014 | Goldfarb | A61H 1/0262 601/35 |
| 2015/0196449 | A1* | 7/2015 | Ahn | A61F 2/68 623/27 |
| 2015/0366740 | A1* | 12/2015 | Endo | A61H 1/0244 623/24 |
| 2018/0092761 | A1* | 4/2018 | Rouse | A61F 2/6607 |
| 2018/0193172 | A1* | 7/2018 | Smith | A61F 2/64 |
| 2019/0070059 | A1* | 3/2019 | Dalley | A61B 5/1117 |

OTHER PUBLICATIONS

Elery, T., et al., "Design and Benchtop Validation of a Powered Knee-Ankle Prosthesis with High-Torque, Low-Impedance Actuators," IEEE International Conference on Robotics and Automation, May 21-25, 2018, 9 pages.

\* cited by examiner

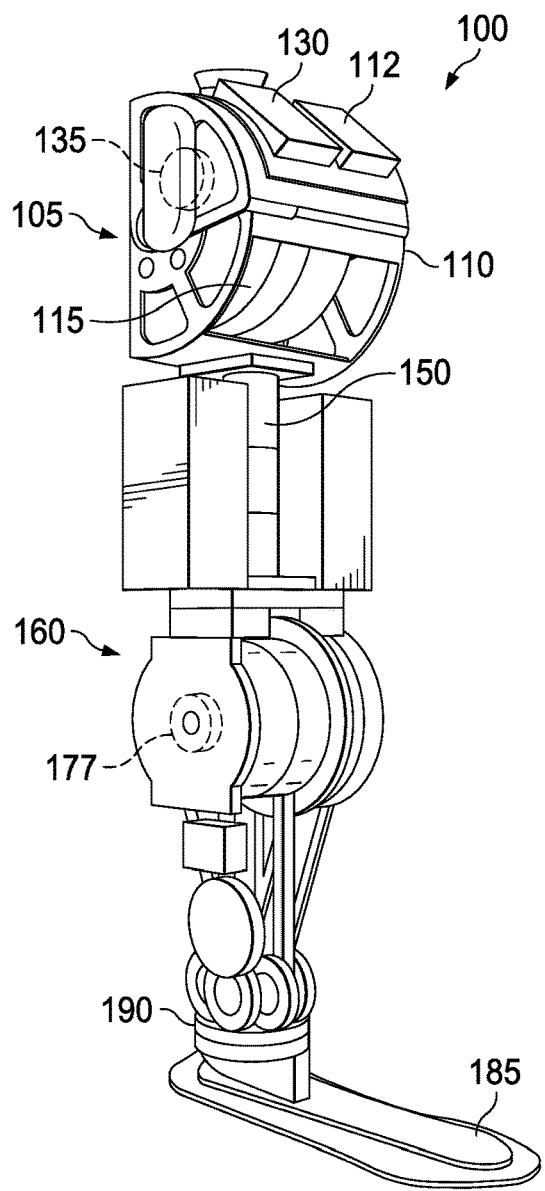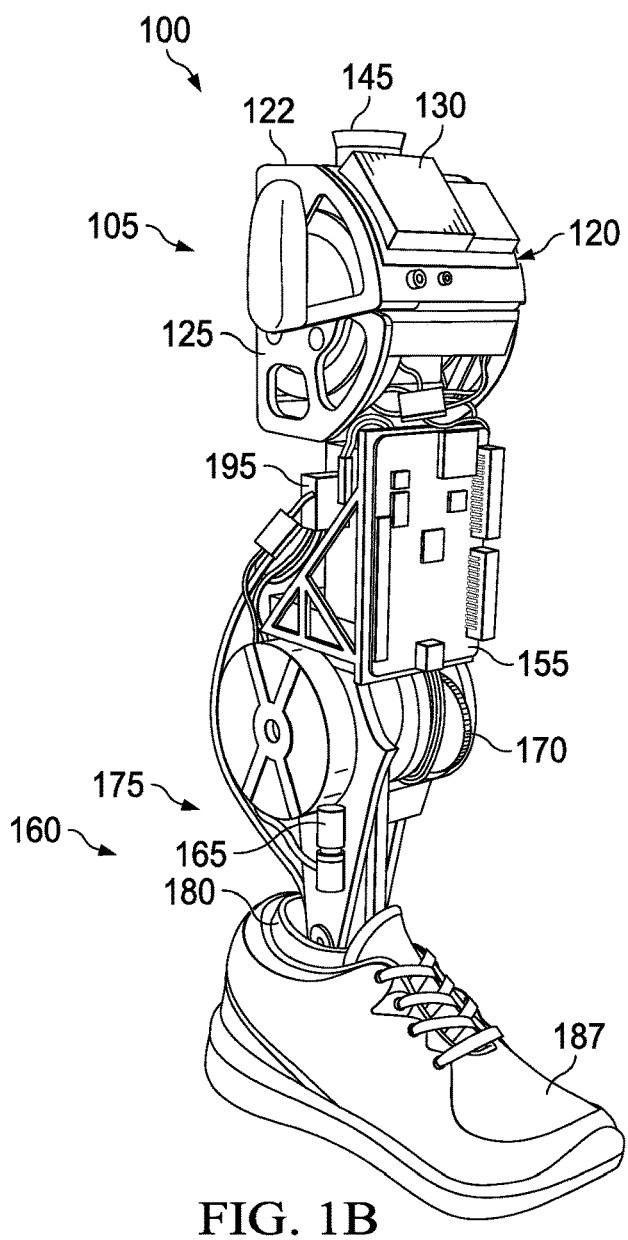
FIG. 1A
FIG. 1B

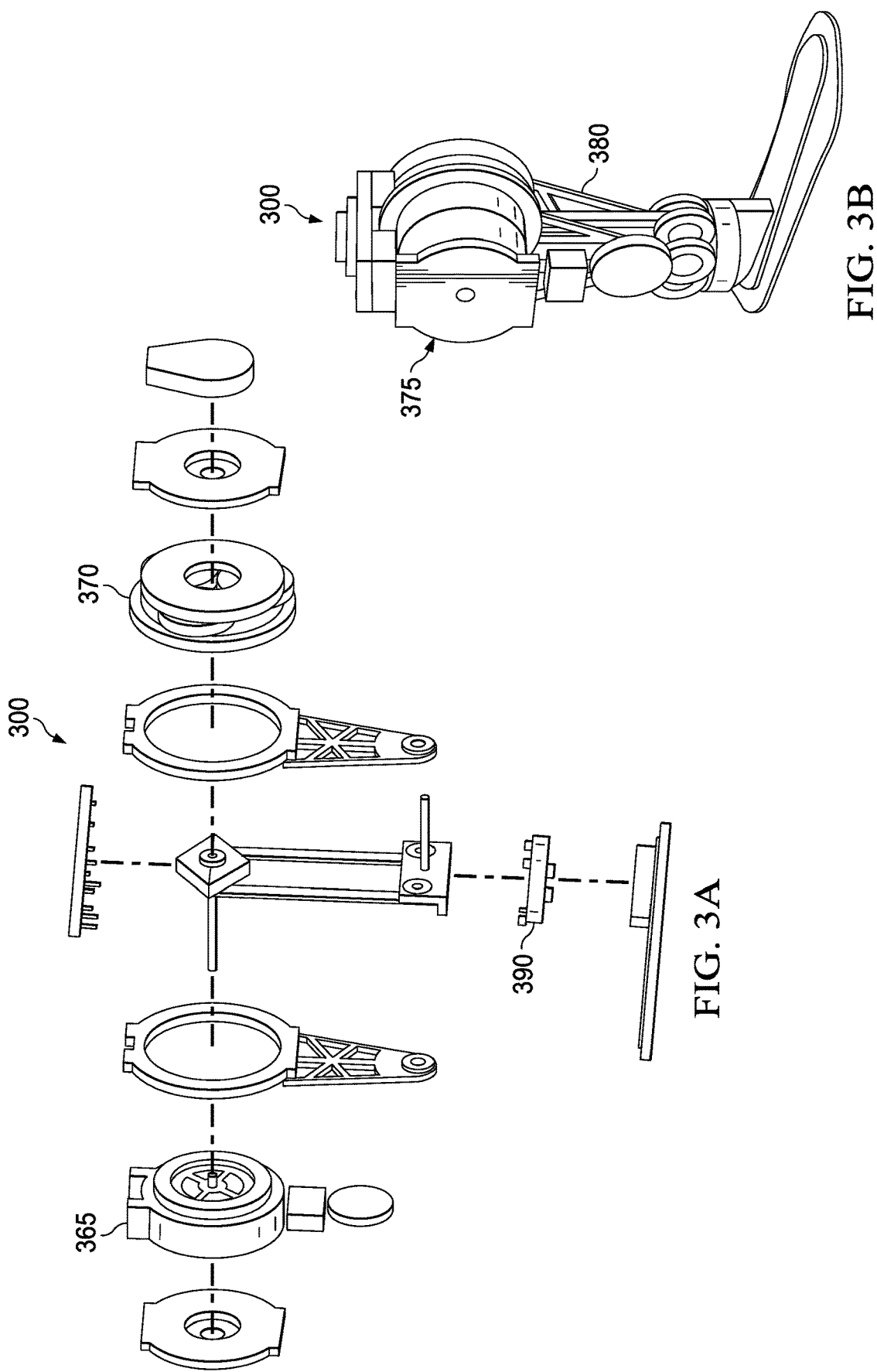

| | ANKLE REQUIREMENTS | KNEE REQUIREMENTS |
|---|---|---|
| TORQUE | 140 Nm | 115 Nm |
| VELOCITY | 360°/s | 330°/s |
| POSITION | -28° TO 20° | 0° TO 105° |
| POWER | 307 W | 225 W |

| | WEIGHT (kg) |
|---|---|
| MOTORS | 1.18 |
| TRANSMISSIONS | 1.39 |
| TORQUE SENSORS | 0.38 |
| LOAD CELL | 0.19 |
| STRUCTURE | 2.29 |
| CF FOOT | 0.30 |
| ELECTRONICS | 0.29 |
| WIRING | 0.03 |
| LI-PO BATTERIES | 0.56 |
| TOTAL | 6.61 |

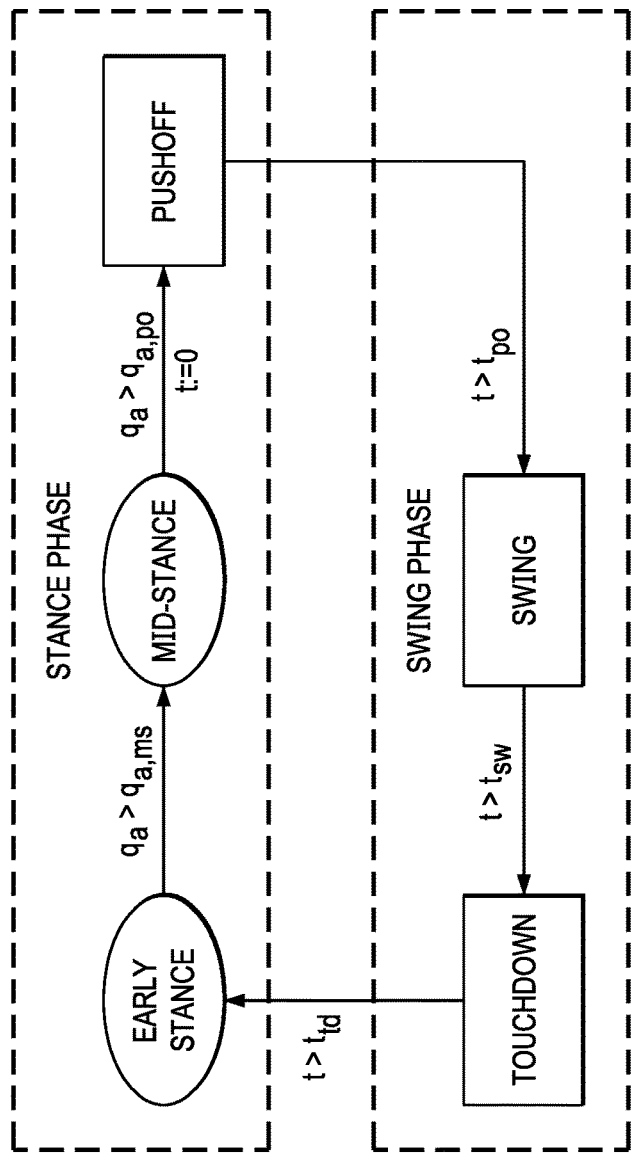
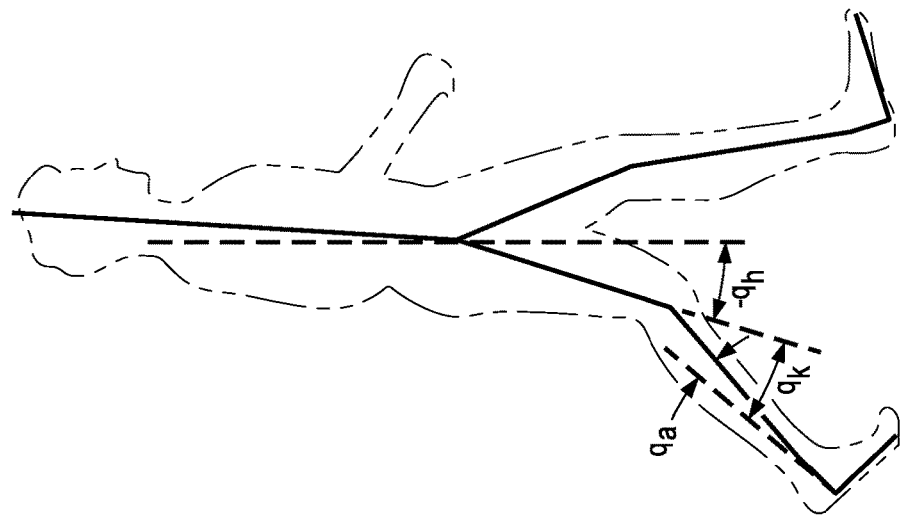
FIG. 7A
FIG. 7B

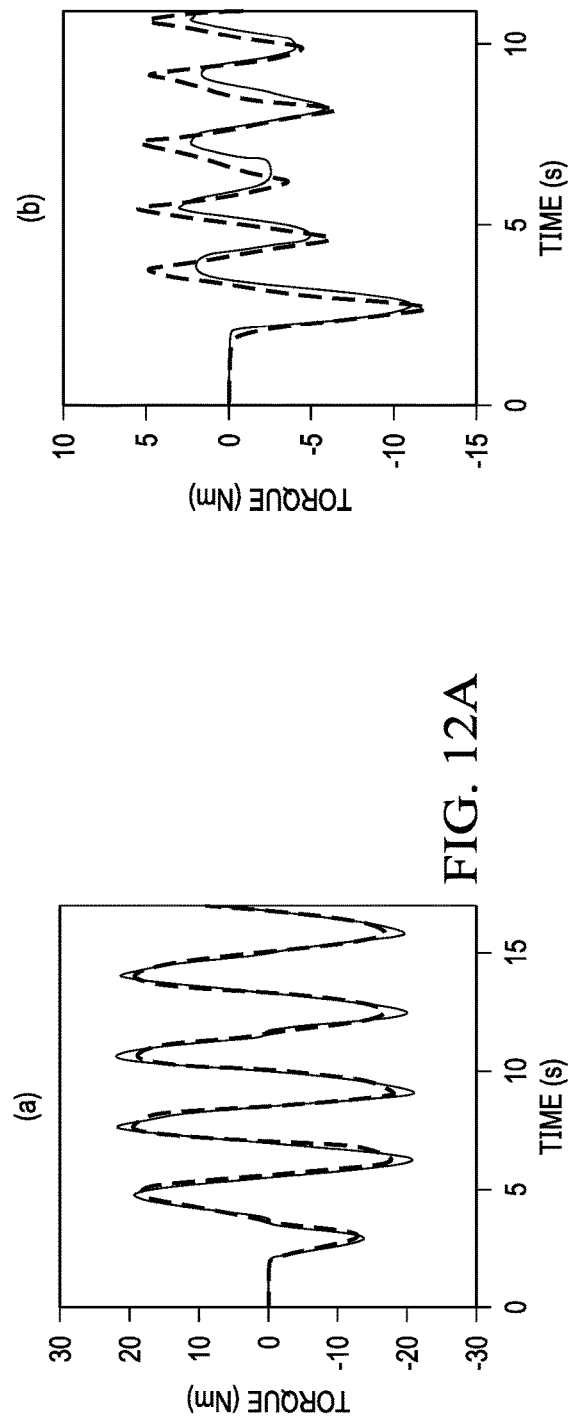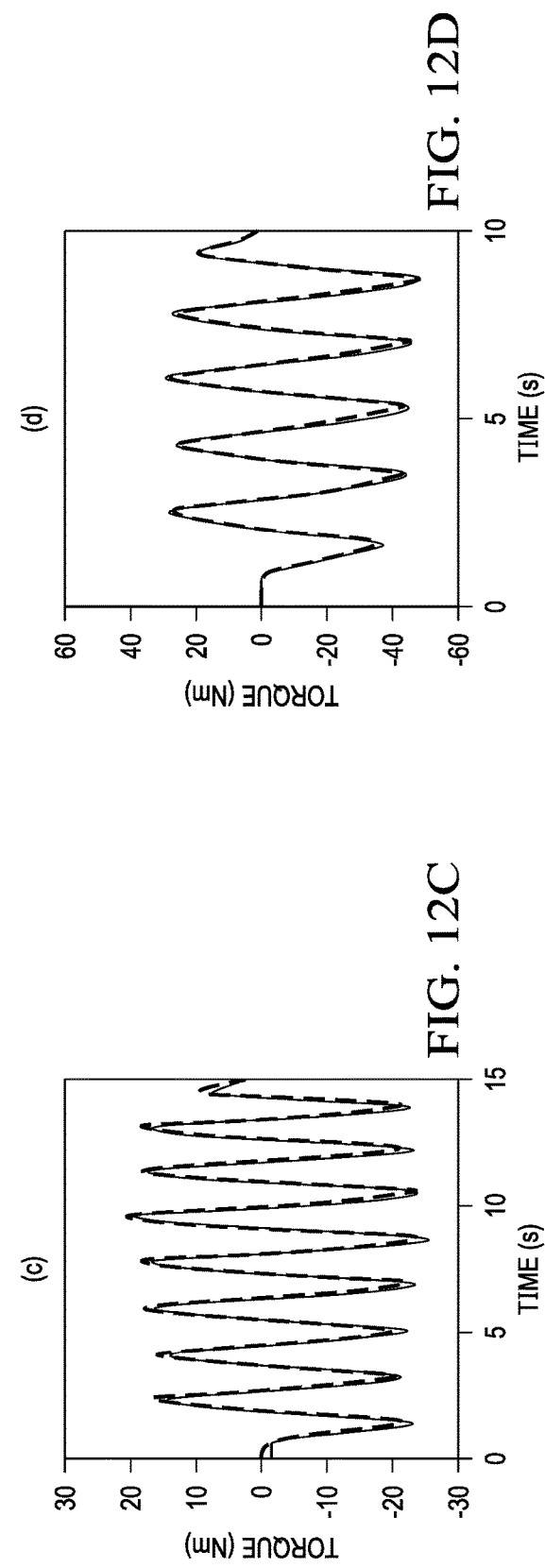
FIG. 12A
FIG. 12B
FIG. 12C
FIG. 12D

| | $K_p$ (ANKLE) | $K_d$ (ANKLE) | $\theta_d$ (ANKLE) | $K_p$ (KNEE) | $K_d$ (KNEE) | $\theta_d$ (KNEE) | $q_{a,ms}$ |
|---|---|---|---|---|---|---|---|
| EARLY STANCE | 246 | 11 | 0 | 284 | 11 | 0.09 | - |
| MID-STANCE | 992 | 17 | 0.07 | 284 | 11 | 0.09 | 0.07 |
| PUSHOFF | - | 17 | TIME-BASED | 458 | 11 | TIME-BASED | - |
| SWING | 688 | 17 | TIME-BASED | 573 | 23 | TIME-BASED | - |

FIG. 14A

| | $K_p$ (ANKLE, PUSHOFF) | $q_{a,po}$ | $t_{po}$ | $t_{sw}$ | $t_{td}$ |
|---|---|---|---|---|---|
| 0.9 m/s | 344 | 0.14 | 0.55 | 0.86 | 0.95 |
| 1.1 m/s | 401 | 0.13 | 0.47 | 0.74 | 0.82 |
| 1.3 m/s | 458 | 0.12 | 0.40 | 0.63 | 0.70 |
| 1.6 m/s | 458 | 0.11 | 0.30 | 0.54 | 0.60 |

FIG. 14B

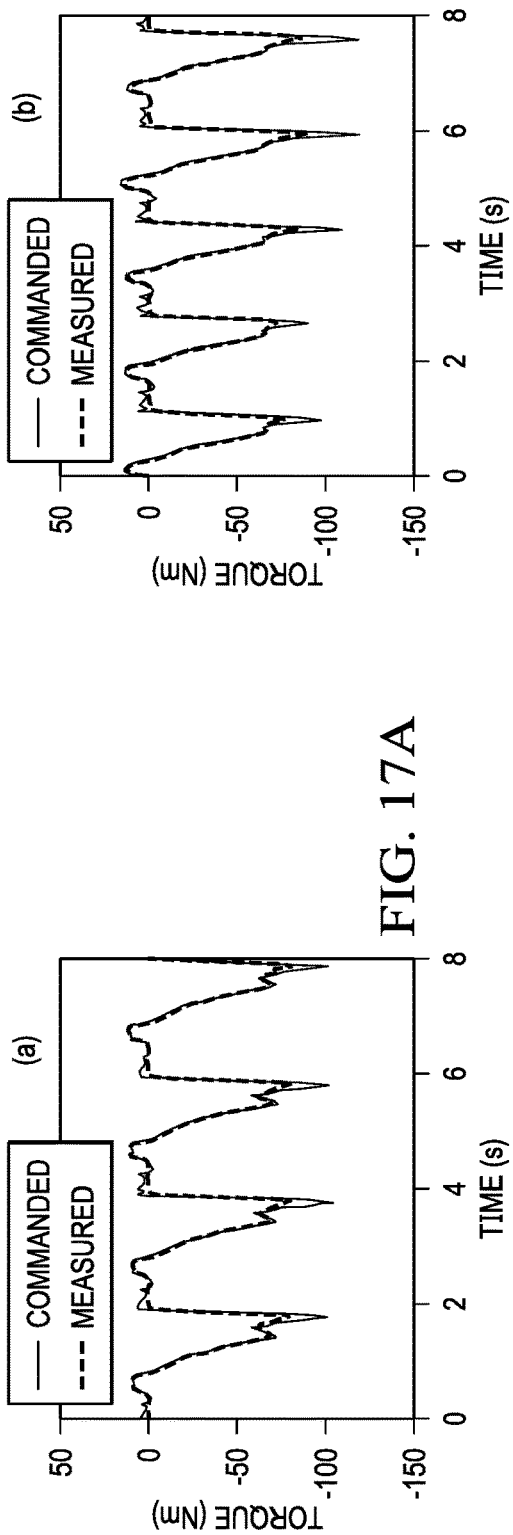
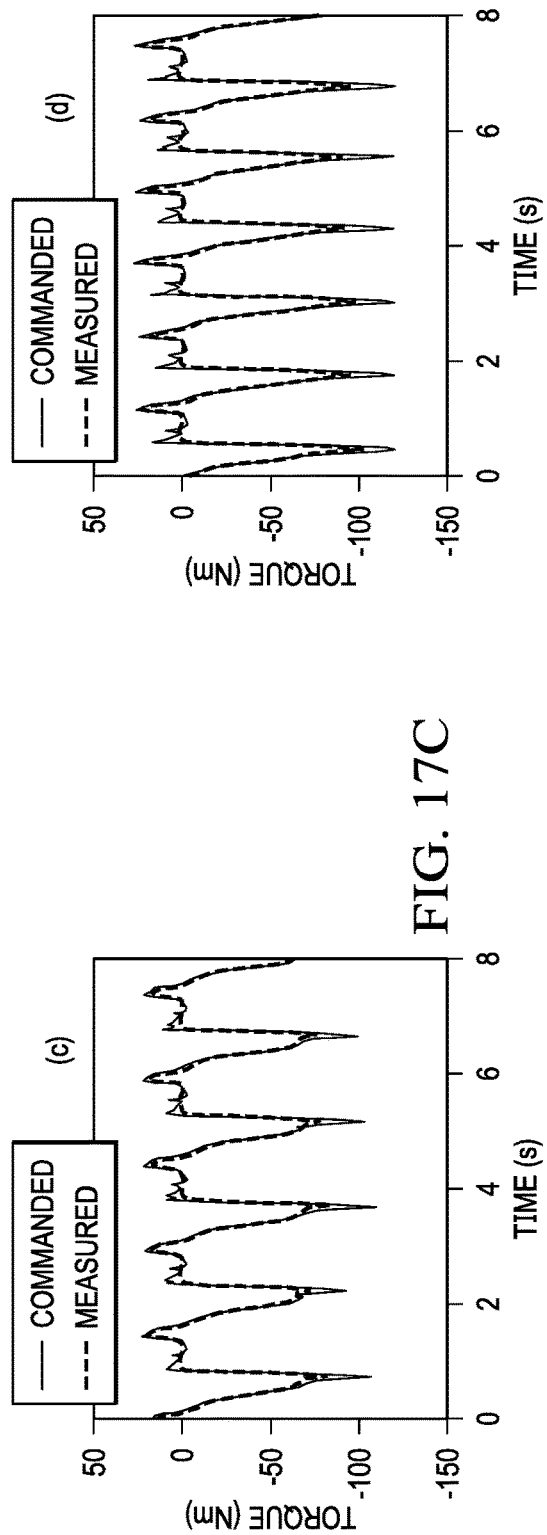
FIG. 17A
FIG. 17B
FIG. 17C
FIG. 17D

| | $E_{P_K}$ (J) | $E_{R_K}$ (J) | $E_{P_A}$ (J) | $E_{R_A}$ (J) | $E_{mech}$ (J) | $E_{batt}$ (J) | $\eta$ (%) |
|---|---|---|---|---|---|---|---|
| 0.9 m/s | 32.8 | -5.1 | 36.9 | -15.2 | 49.5 | 120.0 | 41.2 |
| 1.1 m/s | 30.7 | -5.3 | 35.3 | -11.0 | 49.7 | 97.5 | 51.0 |
| 1.3 m/s | 47.3 | -5.4 | 35.4 | -9.2 | 68.0 | 102.7 | 66.3 |
| 1.6 m/s | 62.3 | -5.0 | 36.9 | -5.4 | 88.8 | 125.4 | 70.9 |
FIG. 19
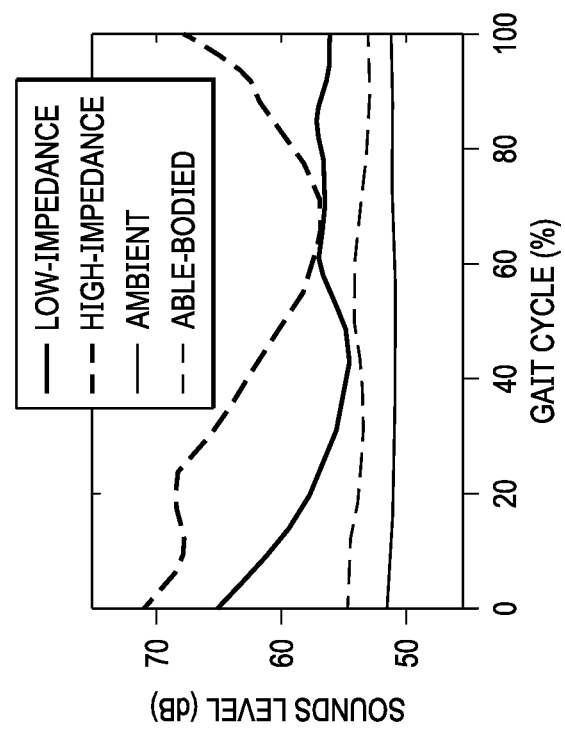
FIG. 20B
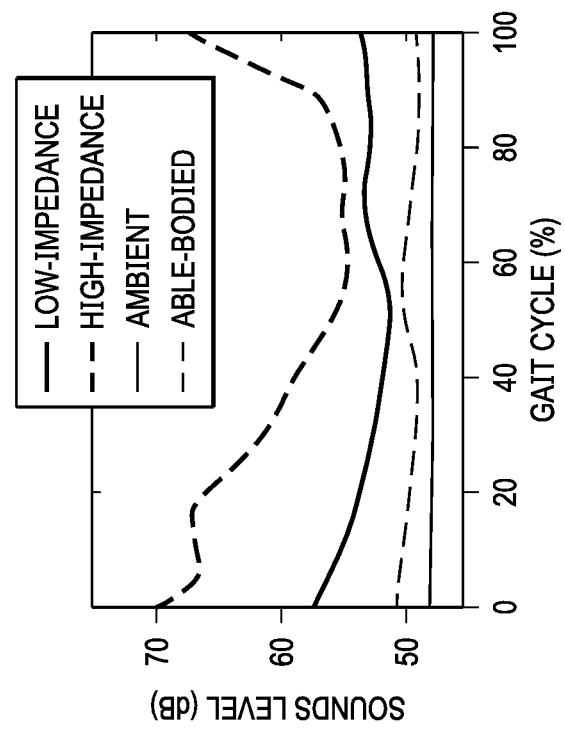
FIG. 20A

| | MOTOR | MOTOR INERTIA $10^{-4}$ (kg·m$^2$) | GEAR RATIO | ROTOR REFLECTED INERTIA AT THE JOINT (kg·m$^2$) | PEAK JOINT TORQUE (N·m) |
|---|---|---|---|---|---|
| LOW-IMPEDANCE LEG - KNEE AND ANKLE | ROBODRIVE ILM 85x26 | 1.1500 | 22:1 | 0.0557 | 183 |
| UTD LEG 1 - KNEE[1] [14] | MAXON EC-4 POLE 30 | 0.0333 | 360:1 | 0.4316 | 40 |
| UTD LEG 1 - ANKLE[1] [14] | MAXON EC-4 POLE 30 | 0.0333 | 720:1 | 1.7263 | 120 |
| VANDERBILT LEG GEN. 3 - KNEE [16] | MAXON EC-4 POLE 30 | 0.0333 | 176:1 | 0.1032 | 85 |
| VANDERBILT LEG GEN. 3 - ANKLE [16] | MAXON EC-60 | 1.1950 | 115:1 | 1.5804 | 110 |
| OPEN-SOURCE LEG - KNEE [26] | T-MOTOR U8 | 1.3000 | 49.4:1 | 0.3172 | 140 |
| OPEN-SOURCE LEG - ANKLE[1] [26] | T-MOTOR U8 | 1.3000 | 58.4:1 | 0.4434 | 165 |
| AMPRO [66] | MOOG BN34 | 0.0510 | 80:1 | 0.3264 | 170 |
| CMU LEG [67] | ROBODRIVE ILM 85-13HS | 0.6100 | 50:1 | 0.1525 | 170 |

FIG. 21

POWERED PROSTHESIS WITH TORQUE DENSE, LOW RATIO ACTUATION

CROSS REFERENCE TO RELATED APPLICATION

This application claims the benefit of U.S. Provisional Application Ser. No. 62/664,655, filed on Apr. 30, 2018, entitled "POWERED KNEE-ANKLE PROSTHESIS WITH TORQUE DENSE, LOW RATIO ACTUATION," commonly assigned with this application and incorporated herein by reference.

GOVERNMENT LICENSE RIGHTS

This invention was made with government support under HD080349 awarded by the National Institutes of Health. The government has certain rights in this invention.

TECHNICAL FIELD

This application is directed, in general, to powered prostheses and, more specifically, to powered prostheses using high torque motors with low-ratio transmissions.

BACKGROUND

Ambulation using a passive prosthesis after the amputation of a lower limb results in a gait that is slower, less stable, and less energy efficient than able-bodied locomotion. Passive prostheses aim to alleviate the effects of amputation using mechanisms such as springs, cams, and dampers to mimic normative gait patterns. However, passive prostheses are limited in functionality due to the fact that such mechanisms can only dissipate energy that the user introduces. Although passive devices restore some functionality, amputees are typically left with an asymmetric gait. Passive prostheses are also limited in their functionality across tasks. For example, many passive devices aim to mimic normal walking conditions. However, this does not address tasks such as sit-to-stand or stair ascent/descent. Semi-active prostheses, such as, e.g., the Ottobock C-Leg, aim to resolve this by utilizing microprocessors to control the damping of joints with the use of small actuators that vary hydraulic valves during the user's gait. This approach allows for a single product to be easily adaptable to a variety of subjects, environments, and tasks. However, since this type of system only actively controls the damping at joints, it is an energy dissipating device, therefore not injecting any energy into the user's gait. What is needed is a powered prosthesis capable of actively injecting energy into the user's gait, which may have the capability to restore mobility and quality of life to those who live with the loss of a limb.

BRIEF DESCRIPTION

Reference is now made to the following descriptions taken in conjunction with the accompanying drawings, in which:

FIGS. 1A and 1B illustrate embodiments of a powered prosthesis according to principles of the disclosure;

FIGS. 3A and 3B are an exploded and assembled view of one embodiment of a second joint actuator which may be used in embodiments of a powered prosthesis according to the disclosure;

Figures 4A, 4B, 4C:
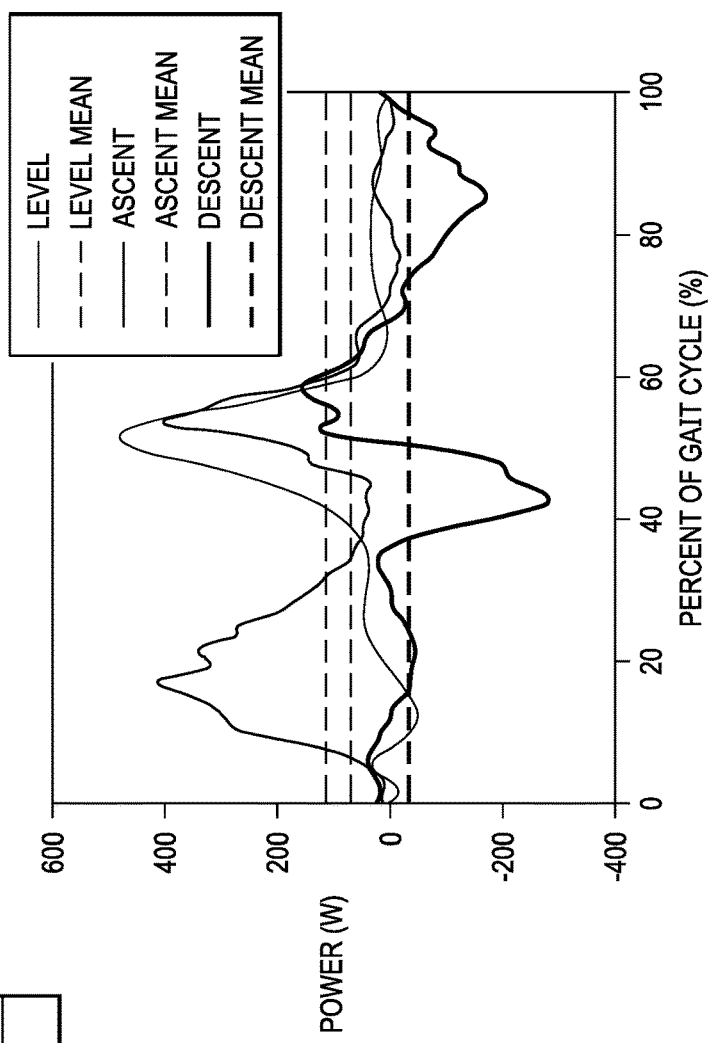
Figure 5A:
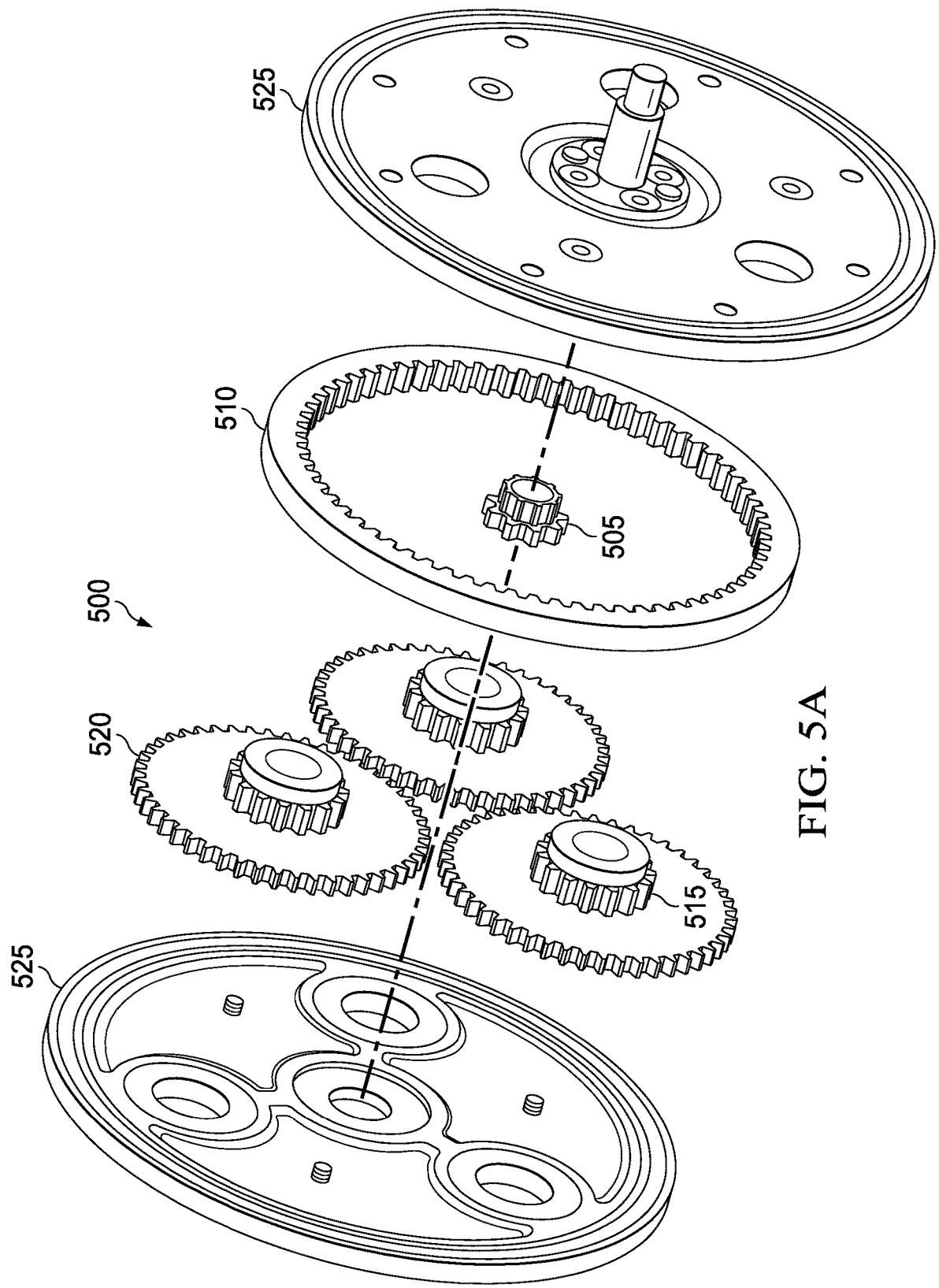
Figure 5B:
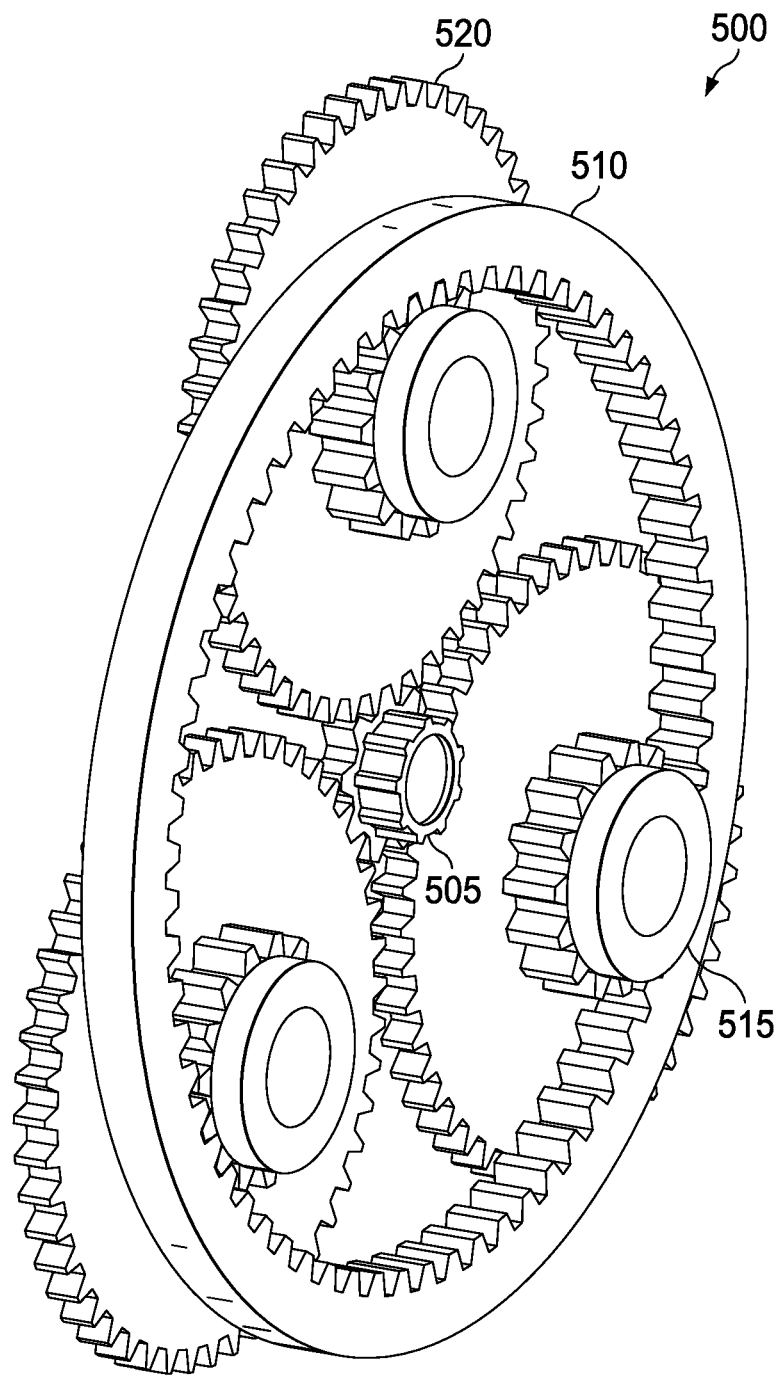
Figure 6:
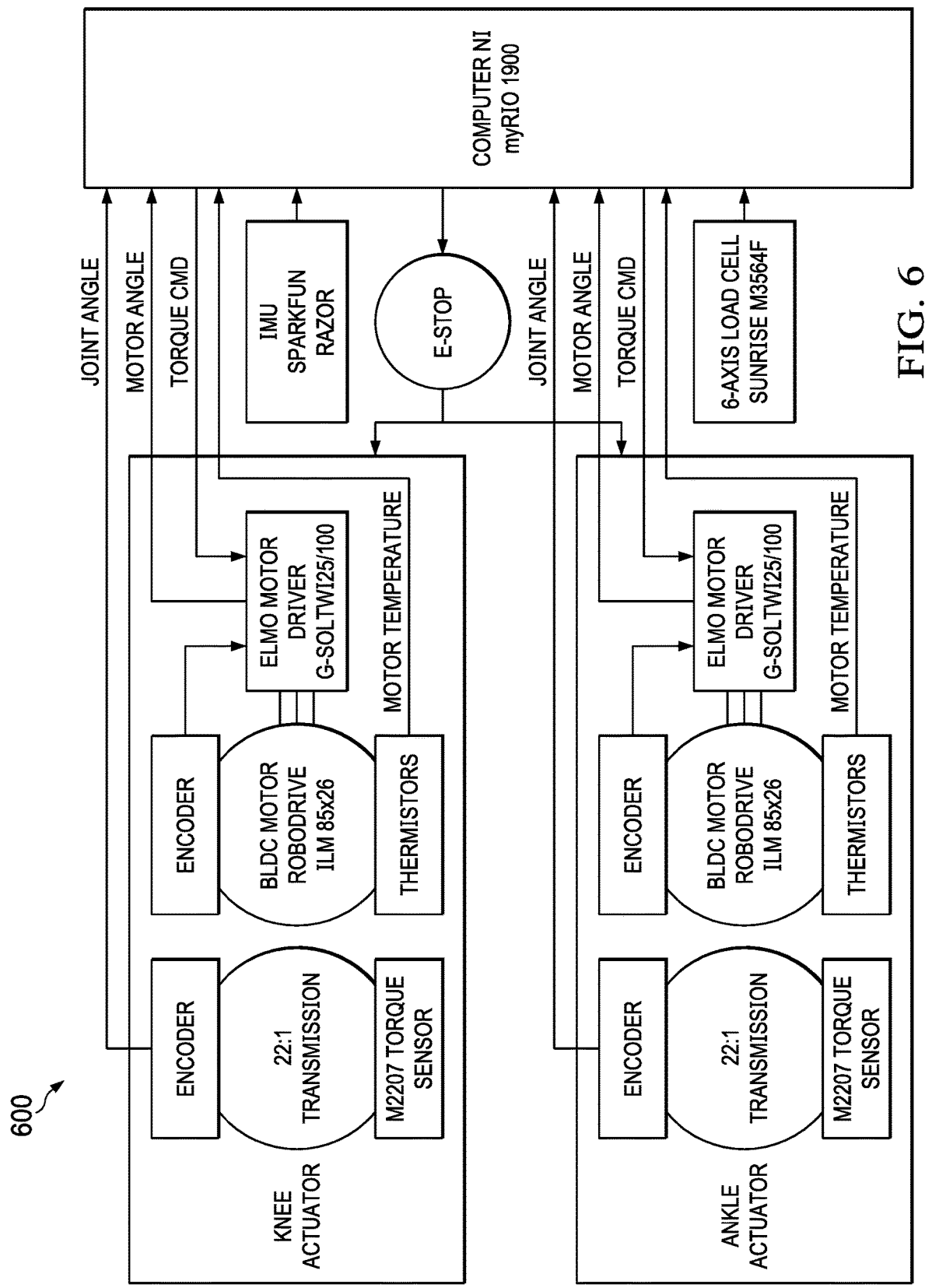
Figure 9:
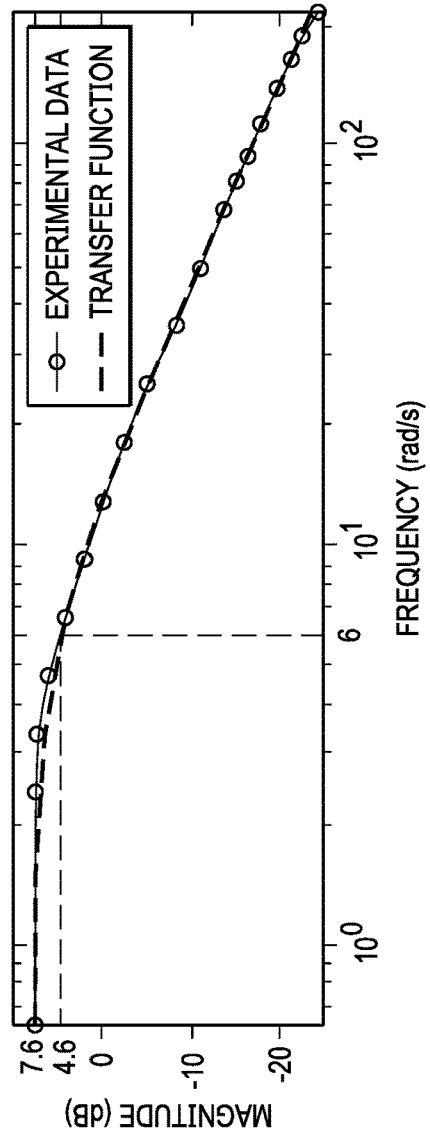
Figure 10:
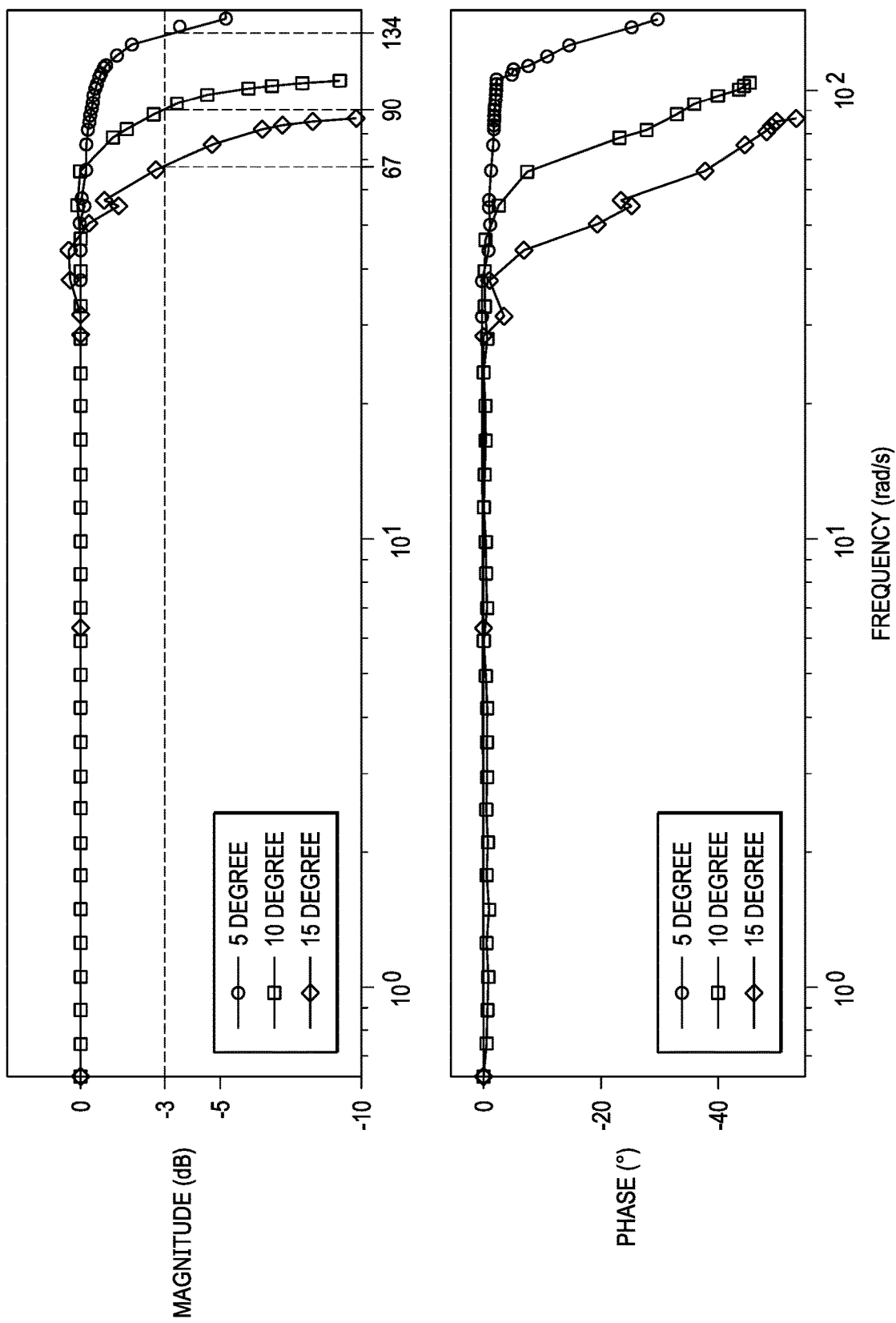
Figure 11A:
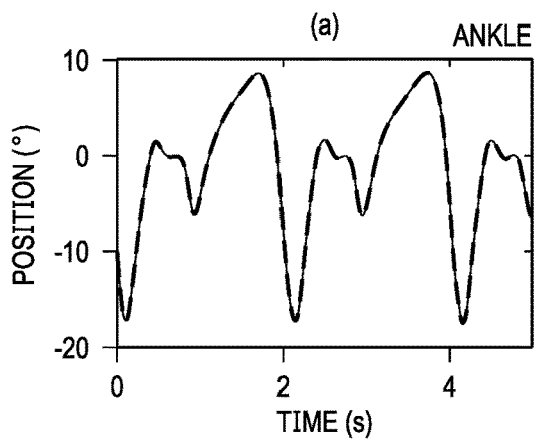
Figure 11B:
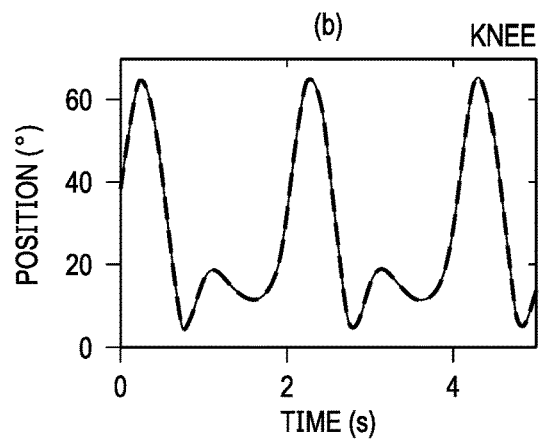
Figure 11C:
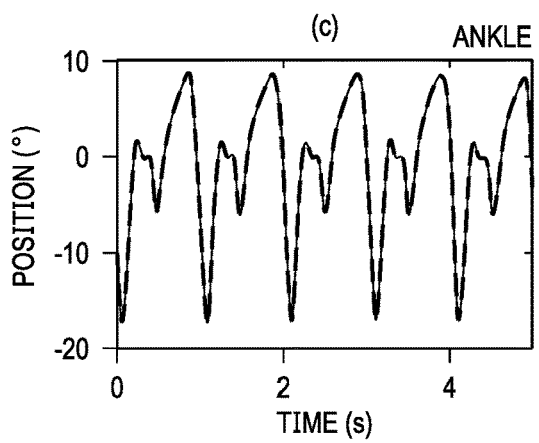
Figure 11D:
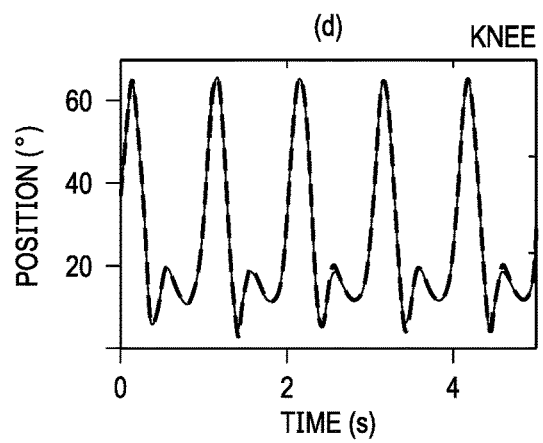
Figure 11E:
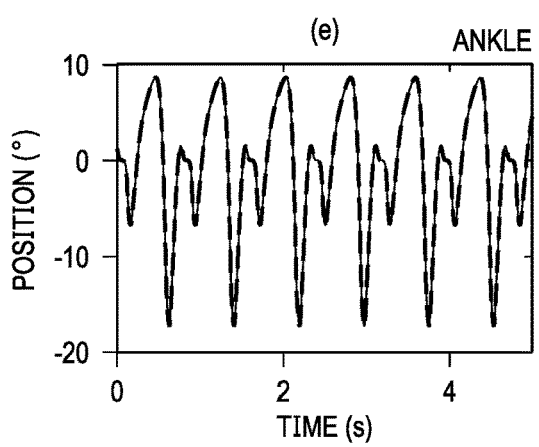
Figure 11F:
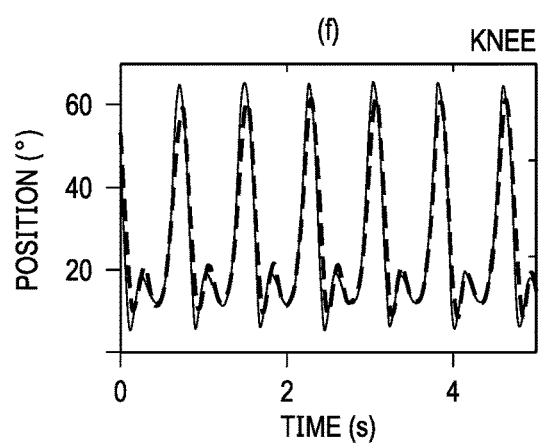
Figure 13A:
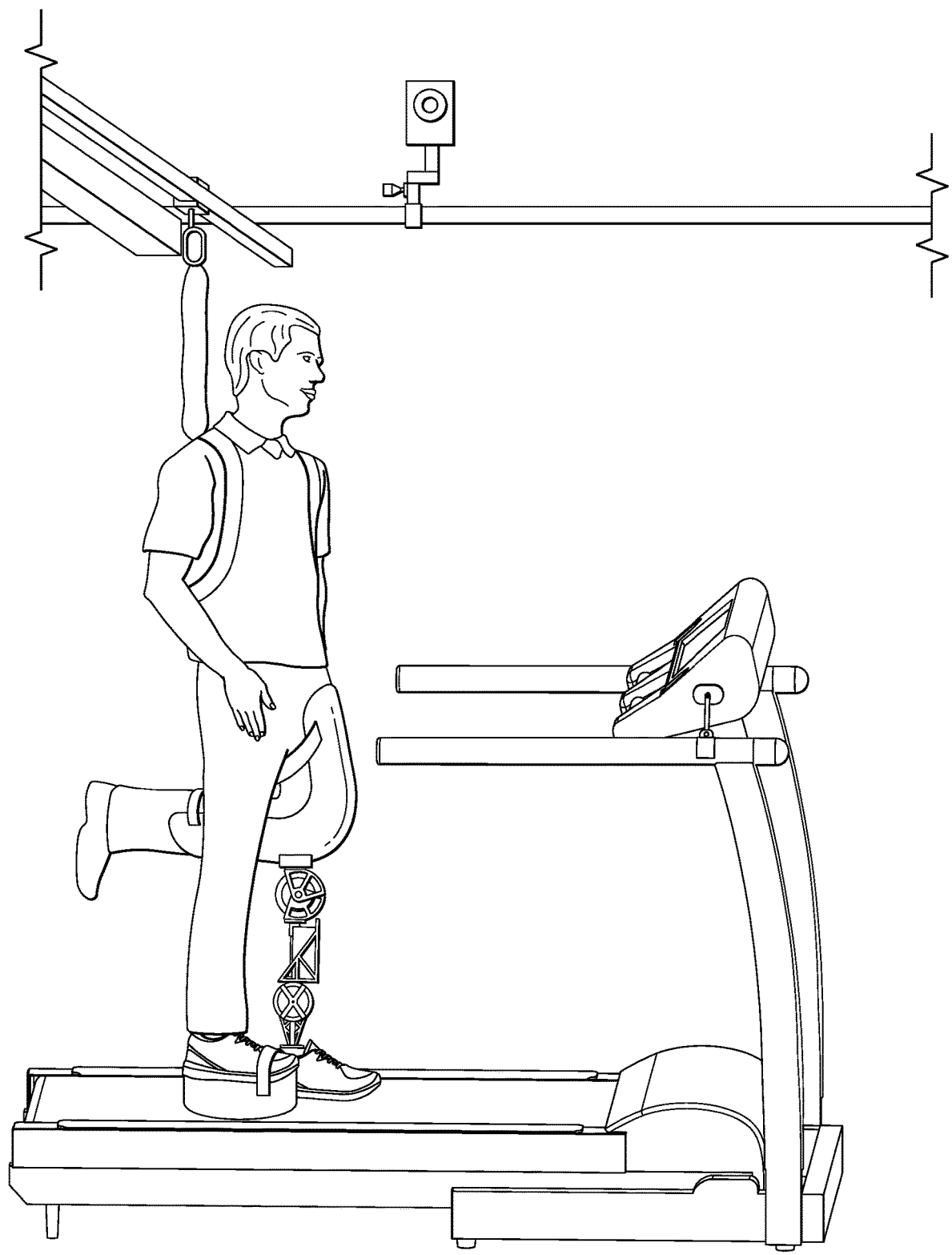
Figure 13B:
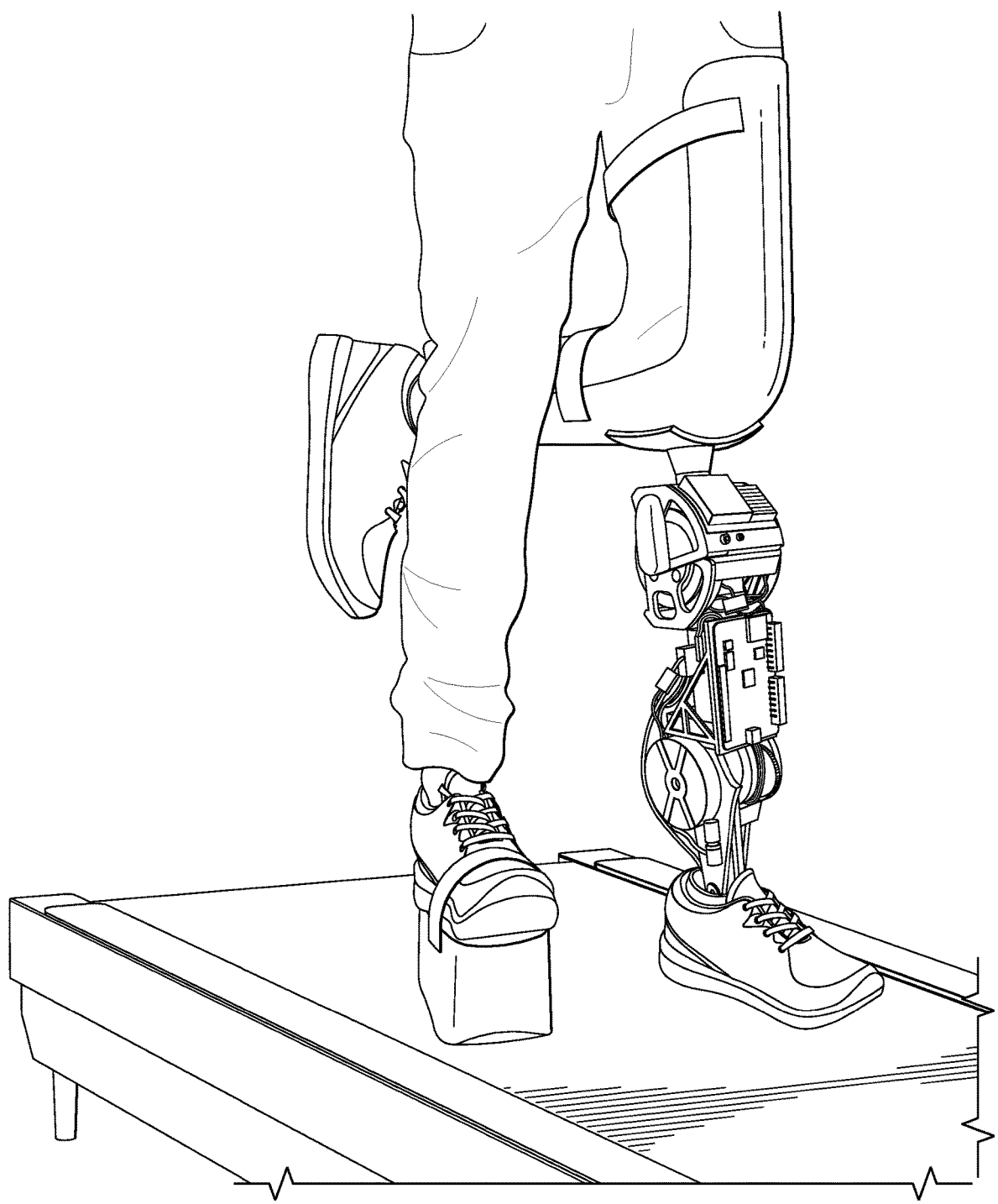
Figure 15A:
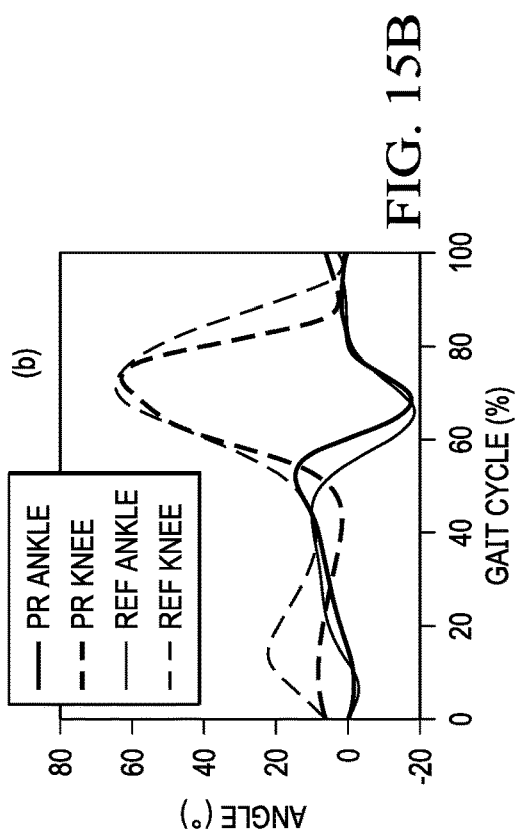
Figure 15B:
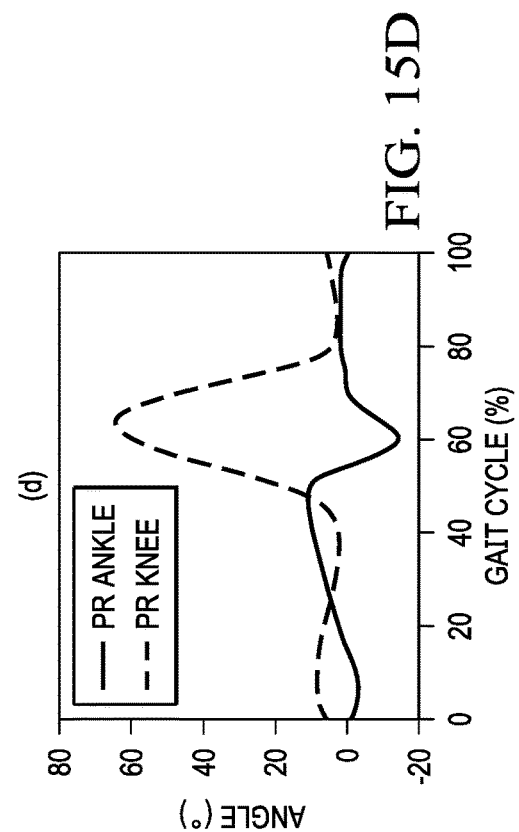
Figure 15C:
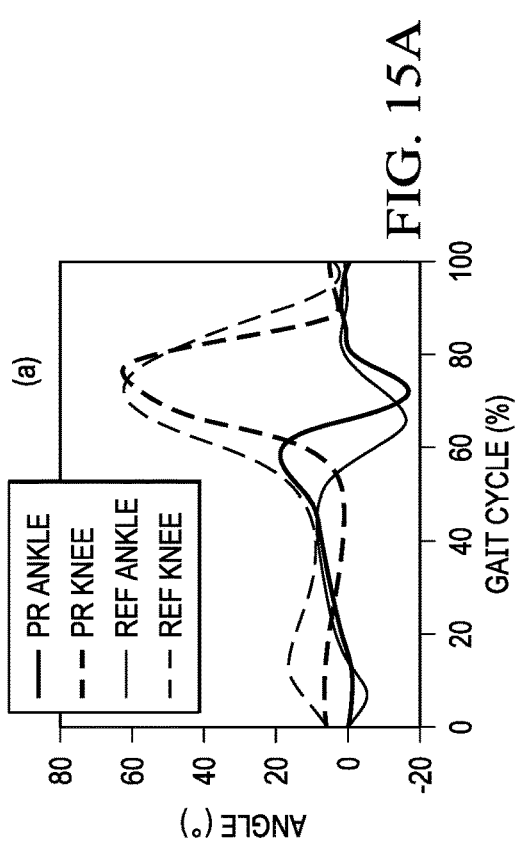
Figure 15D:
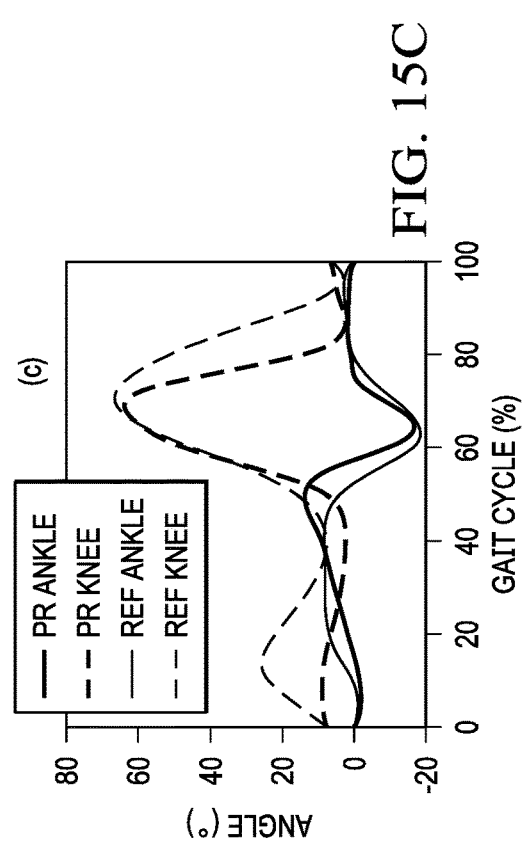
Figure 16A:
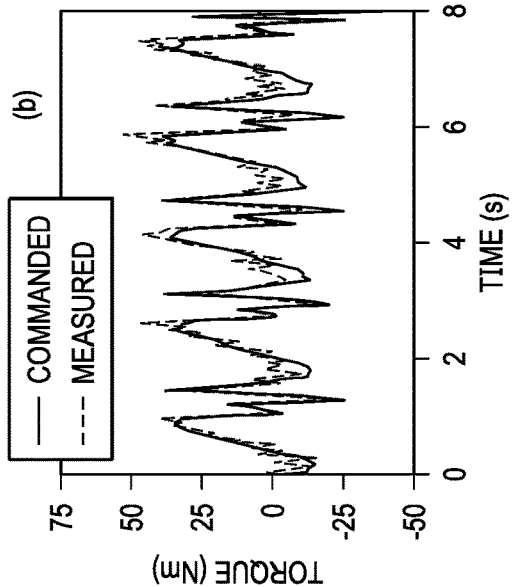
Figure 16B:
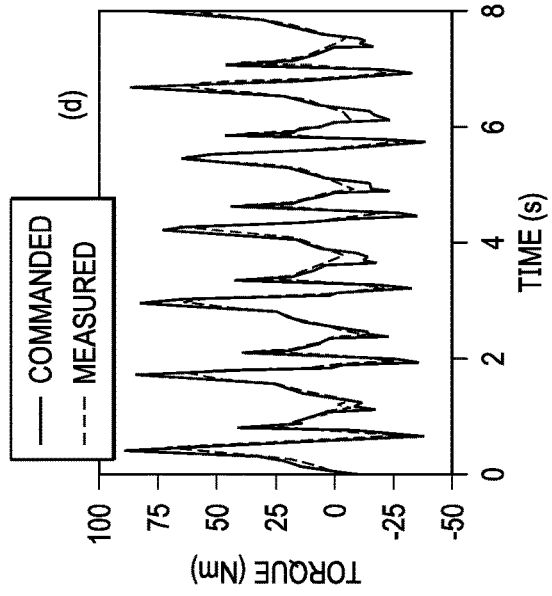
Figure 16C:
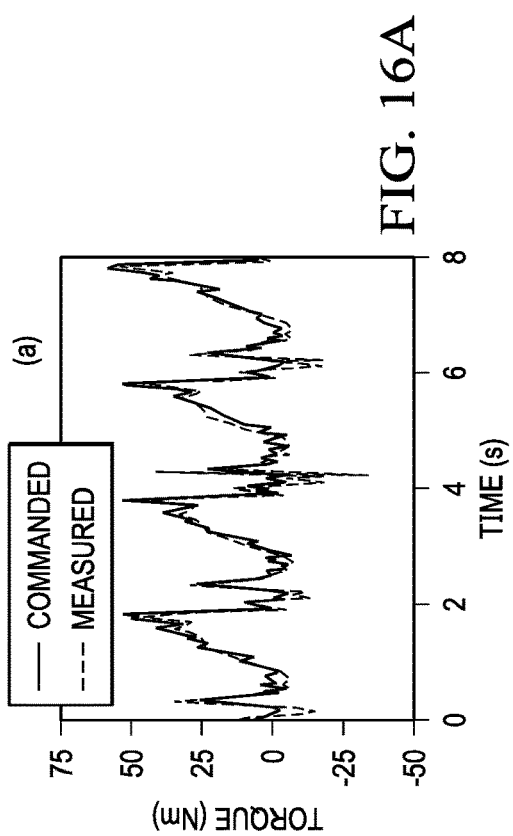
Figure 16D:
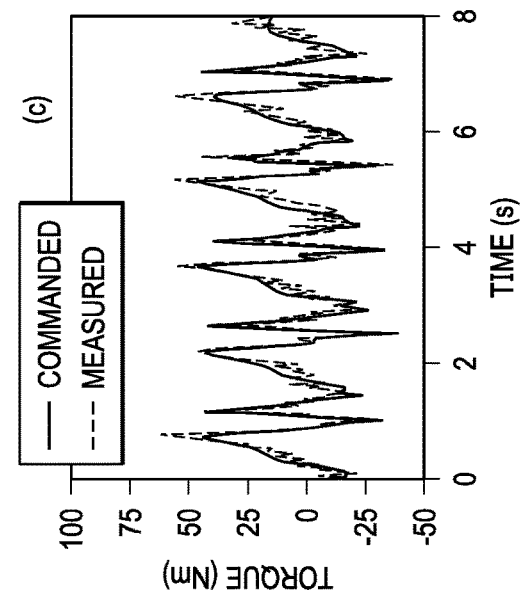
Figure 18A:
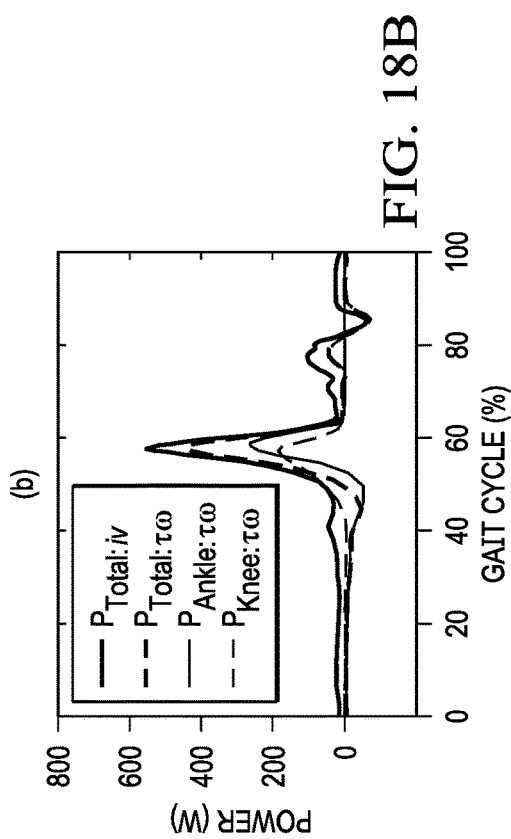
Figure 18B:
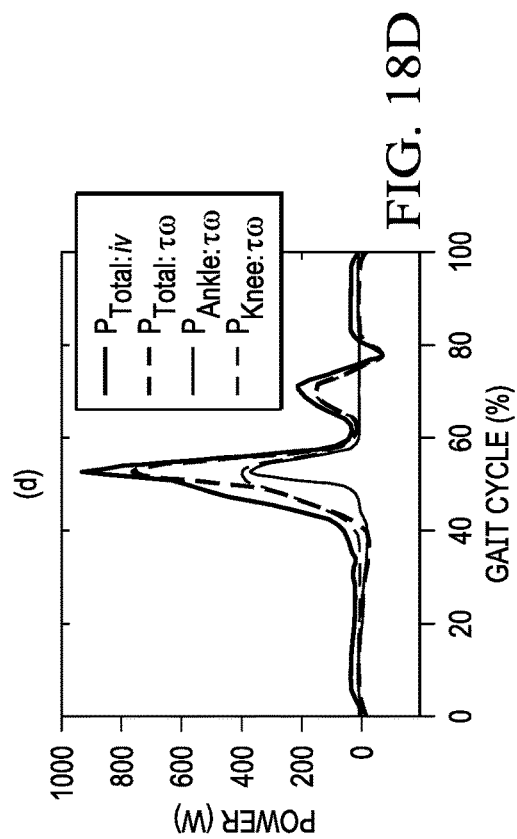
Figure 18C:
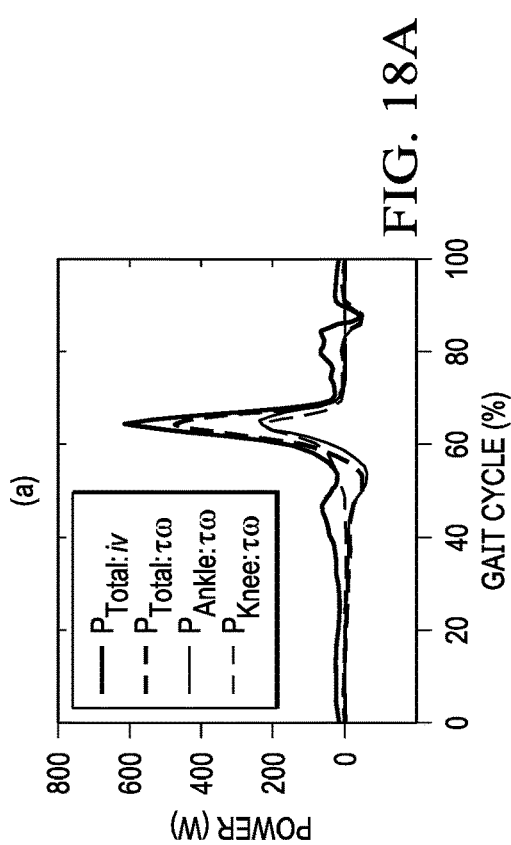
Figure 18D:
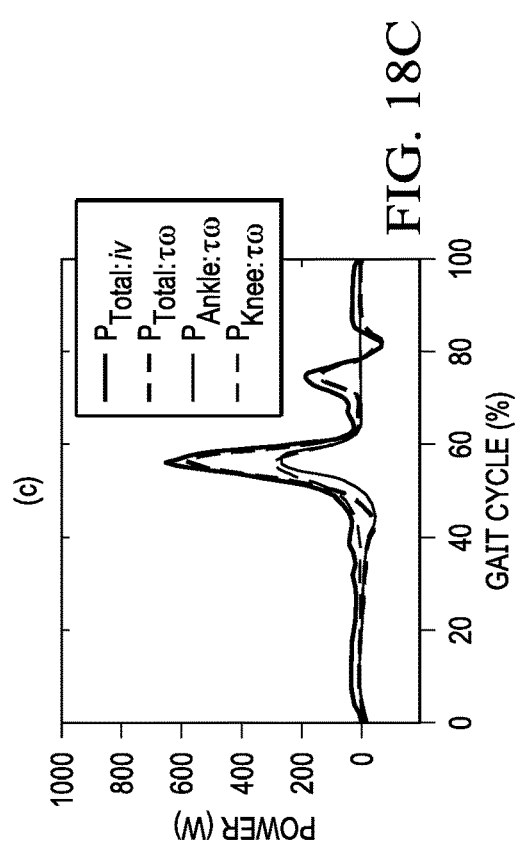

FIGS. 4A-4C Tables and a Diagram illustrating power and weight requirements determine for certain embodiments of a powered prosthesis according to the disclosure;

FIGS. 5A and 5B illustrate an exploded and assembled view of one of a gear system which may be used in embodiments of a powered prosthesis according to the disclosure;

FIG. 6 is a diagram of an electrical and control system that may be used in embodiments of a powered prosthesis according to the disclosure;

FIGS. 7A and 7B illustrate a finite state machine walking test for one embodiment of a prosthesis according to the principles of the disclosure;

FIGS. 8A-8D illustrate views and results of testing experiment to quantify backdrive torque and free-swing capabilities of first and second joint actuators of embodiments of a prosthesis according to the disclosure;

FIG. 9 illustrates testing results for an open loop velocity bandwidth test performed using features of a powered prosthesis according to the principles of the disclosure;

FIG. 10 illustrates closed loop position bandwidth tests illustrating how one embodiment of a prosthesis according to the disclosure may track human-like joint positions;

FIGS. 11A-11F illustrate testing results for gait trajectories at various frequencies performed using features of a powered prosthesis according to the principles of the disclosure;

FIGS. 12A-12D illustrate testing results for open loop impedance testing performed using features of a powered prosthesis according to the principles of the disclosure;

FIG. 13 illustrates a walking experiment with one embodiment of a powered prosthesis according to the principles of the disclosure;

FIG. 14A is a table showing speed-independent control parameters from analysis of the walking experiment illustrated in FIG. 13;

FIG. 14B is a table showing speed-dependent control parameters from analysis of the walking experiment illustrated in FIG. 13;

FIGS. 15A-15D illustrate joint actuator positions during gait from testing analysis using one embodiment of a powered prosthesis according to the principles of the disclosure;

FIGS. 16A-16D illustrate commanded and measured torque of a first joint actuator from testing analysis using one embodiment of a powered prosthesis according to the principles of the disclosure;

FIGS. 17A-17D illustrate commanded and measured torque of a second joint actuator from testing analysis using one embodiment of a powered prosthesis according to the principles of the disclosure;

FIGS. 18A-18D illustrate average power per gait cycle from testing analysis using one embodiment of a powered prosthesis according to the principles of the disclosure;

FIG. 19 is a table illustrating average energy efficiency per gait cycle from testing analysis using one embodiment of a powered prosthesis according to the principles of the disclosure;

FIGS. 20A and 20B illustrate acoustic sound level results from testing analysis using one embodiment of a powered prosthesis according to the principles of the disclosure; and FIG. 21 illustrates a Table comparing inertias, transmission ratios, and joint torque of joint actuators in the prostheses according to principles of the disclosure with other prostheses.

DETAILED DESCRIPTION

In the last decade, a great amount of research has gone into the design and control of powered prosthetic limbs. Many powered prosthetic devices have emerged from this research, several of which implement non-backdrivable joint actuators, consisting of high-speed, low-torque motors with high-ratio transmissions, such as ball screws or multiple gear stages. In the past few years, legged robots such as the quadruped MIT Cheetah, biped ATRIAS, and others have embraced high-torque motors with low-ratio or no transmissions. As a result, certain exoskeletons in the field of rehabilitation robotics have recently implemented high-torque motors in combination with low-ratio transmissions.

High-torque, low-reduction-ratio actuators can have several benefits for control and efficiency of robotic legs. Lower mechanical impedance (inertias and frictional losses), which may characterize some of these joint actuators may minimize the effect of unmodeled dynamics, which in turn may help simplify an otherwise complex control problem, increasing robustness, and forcing the system to behave closer to an ideal model. Force control in these joint actuators can be comparable to or better than series elastic actuators without their design and manufacturing complexities. Other benefits may include passive knee-swing motion, potential for power regeneration, and compliance with the ground through impedance control. A free-swinging knee joint actuator, in one embodiment allows for a more natural gait, while reducing the power requirements of the joint actuator during swing phase. Power regeneration phases of negative work on the leg, including swing knee extension, can lead to longer periods of untethered operation, which is critical for robotic legs. Further, compliance with the ground provides a smoother touchdown impact, which can in turn improve efficiency of the system and comfort for the user.

In the process of designing low-impedance actuators, transmission design is a critical problem. Single-stage planetary transmissions, in some embodiments, may be extremely efficient and have less intrinsic impedance than multi-stage transmissions, but they are typically limited to ratios below 10:1. Therefore, efficient single-stage transmissions sometimes may require a customized motor design to achieve the high output torques required during legged locomotion. Other transmission choices used in robotic legs such as harmonic and cycloid gear drives exhibit other problems such as efficiency and manufacturing complexities, respectively.

Disclosed herein are embodiments of joint actuators which may be used in a powered prosthesis. Some embodiments of a powered prosthesis may use a single-stage stepped-planet compound planetary gear transmission (SPC-PGT) coupled with a high torque-density motor at one or more joint actuators of the prosthesis. Accordingly, some embodiments of joint actuators may have low mechanical impedance and high back-drivability. In addition, this style of transmission may offer a higher range of reduction ratios while maintaining efficiency and simplifying manufacturing compared to previously mentioned transmissions.

In the disclosure, embodiments of a trans-femoral knee-ankle prosthesis are shown and described for illustration and description purposes, but other embodiments of a powered prosthesis may also include other multi-joint prostheses, including, but not limited to, elbow-wrist prostheses and other multi-joint uses. The powered prosthesis according to the disclosure implements high torque density joint actuators with low-reduction transmissions. The low reduction of the transmission coupled with a high-torque and low-speed motor provides, in some embodiments, a joint actuator with low mechanical impedance and high back-drivability. Embodiments of the powered prosthesis presented herein may provide several possible benefits over modern joint actuation styles implemented in emerging robotic prosthetic legs. Such benefits include, but are not limited to free-swinging knee motion, compliance with the ground, negligible unmodeled actuator dynamics, more accurate torque control, lower acoustic noise than in traditional prostheses, and greater potential for power regeneration. Benchtop validation experiments were conducted to verify some of the foregoing benefits. Results of backdrive and free-swinging knee tests discussed herein show that in some embodiments, both joints may can be backdriven by small torques, such as, e.g., about 3 Nm. Results of bandwidth tests disclosed herein reveal that some embodiments of joint actuators may be capable of achieving frequencies required for walking and running. Further, results of one or more open-loop impedance control tests, presented herein, may show that intrinsic impedance and unmodeled dynamics of some embodiments of joint actuators are sufficiently small to control joint impedance without torque feedback.

This technology, in one embodiment, is a powered prosthesis including at least a first joint actuator and a second joint actuator, in this embodiment, a knee actuator and an ankle actuator, using high torque motors with custom low-ratio transmissions. The high torque joint actuators allow more energy injection into the human gait cycle for more natural locomotion. The low-ratio transmission is highly backdrivable which provides compliance to impacts, natural swinging knee motion, potential to harvest energy, more accurate torque control, lower acoustic noise than in traditional prostheses, and the ability to detect the ground slope. The torque/power capabilities of this prosthetic leg are greater than existing prosthetic legs with similar weight, allowing better performance over a wider range of tasks while minimizing orthopedic strain. In some embodiments, the prosthesis may include torque sensors in both actuators for more accurate torque control.

Presented herein are features of a powered trans-femoral prosthetic leg presented which implements, in one embodiment, a walking controller that utilizes the compliant nature of the leg's joint actuators to facilitate smooth and easy switching between impedance and position control paradigms at different walking speeds. Moreover, the low impedance of the joint actuators allows for the direct use of estimated human joint impedance, which simplifies the implementation of the biomimetic walking controller by eliminating the lengthy tuning process associated with typical impedance control. Examining the leg during walking allows for the quantification of specific properties not measurable during benchtop testing, such as kinematics and kinetics, electrical power, and acoustic sound levels during normative loading conditions. Joint compliance may facilitate energy/power regeneration and power sharing between joint actuators during periods of negative work, such as, e.g., knee swing extension. This is useful to increase the efficiency of powered prostheses, which leads to extended battery life and usage time. Furthermore, embodiments of the prosthesis may provide a reduction in acoustic sound levels that can prevent drawing unwanted attention to a user while ambulating in quiet environments.

For the purpose of the present disclosure and claims, a high output torque motor has a peak output torque (e.g., measured over a 10 second time period) of at least about 1.0 Nm. Similarly, for the purpose of the present disclosure and claims, a very high output torque motor has a peak output torque (e.g., measured over a 10 second time period) of at least about 1.5 Nm, and an extremely high output torque motor has a peak output torque (e.g., measured over a 10 second time period) of at least about 2.0 Nm. Also, for the purpose of the present disclosure and claims, an excessively high output torque motor has a peak output torque (e.g., measured over a 10 second time period) of at least about 4.0 Nm.

For the purpose of the present disclosure and claims, a high torque density motor has a torque density (e.g., a measure of the peak torque output divided by the motor's stator and rotor weight) of at least about 3.3 Nm/kg. Similarly, for the purpose of the present disclosure and claims, a very high torque density motor has a torque density (e.g., a measure of the peak torque output divided by the motor's stator and rotor weight) of at least about 5.0 Nm/kg, and an extremely high torque density motor has a torque density (e.g., a measure of the peak torque output divided by the motor's stator and rotor weight) of at least about 6.7 Nm/kg. Also, for the purpose of the present disclosure and claims, an excessively high torque density motor has a torque density (e.g., a measure of the peak torque output divided by the motor's stator and rotor weight) of at least about 13.3 Nm/kg.

Additionally, for the purpose of the present disclosure and claims, a low-ratio transmission is a transmission with a ratio of 32:1 or less. Similarly, for the purpose of the present disclosure and claims, a very low-ratio transmission is a transmission with a ratio of 24:1 or less, and an extremely low-ratio transmission is a transmission with a ratio of 16:1 or less. Additionally, for the purpose of the present disclosure and claims, an excessively low-ratio transmission is a transmission with a ratio of 12:1 or less.

Similarly, for the purpose of the present disclosure and claims, a device that is backdrivable is a device wherein its static torque (e.g., minimum backdrive torque to begin motion of the motor shaft) is less than about 10 Nm. Likewise, for the purpose of the present disclosure and claims, a device that is very backdrivable is a device wherein its static torque (e.g., minimum backdrive torque to begin motion of the motor shaft) is less than about 5 Nm, and a device that is extremely backdrivable is a device wherein its static torque (e.g., minimum backdrive torque to begin motion of the motor shaft) is less than about 2.5 Nm. Also, for the purpose of the present disclosure and claims, a device that is excessively backdrivable is a device wherein its static torque (e.g., minimum backdrive torque to begin motion of the motor shaft) is less than about 2.0 Nm.

Referring now to FIGS. 1A and 1B there is shown one embodiment of a prosthesis 100 constructed according to the disclosure. FIG. 1A illustrates a CAD rendering of the prosthesis 100 and FIG. 1B shows one embodiment of the prosthesis 100 as assembled. In this embodiment, the prosthesis 100 includes a first joint actuator 105 and a second joint actuator 160, connected by an adjustable connector 150, which in this embodiment, may be an adjustable pylon. The adjustable connector 150 enables the prosthesis 100 to be adjusted and used for potential users of varying heights and sizes. The first joint actuator 105 includes at least a first motor 110 and a first transmission 115. In some embodiments, the first motor 110 and first transmission 115 may be positioned co-axially within a housing 120. In one embodiment, the housing 120 may include a first portion 122, which in this embodiment is a top-hinge portion, and a second portion 125, which in this embodiment is a bottom hinge portion.

The first joint actuator 105 may also include an inertial measurement unit (IMU) and an encoder 135, both positioned in or about the first housing 120. The encoder 135 sends motor position data to a motor driver 112, which may be positioned proximate the first motor 110, and a system controller 155. (Aspects of the system controller will be described below in conjunction with FIG. 6). In some embodiments, the IMU may be positioned near or within the first housing 120. In some embodiments, the IMU may be positioned above the first housing 120. An adapter 145, such as a pyramid adapter may be used to attach the prosthesis with a limb positioned above the prosthesis 100, such as, e.g., a thigh or femur. In such embodiments, the IMU may be used to measure an angle of the limb.

The first motor 110 in some embodiments may be a high output torque motor as described above. In other embodiments, the first motor 110 may be a very high output torque motor, an extremely high output torque motor, or an excessively high output torque motor. Similarly, the first motor 110, in some embodiments, may be a high torque density motor, a very high torque density motor, an extremely high torque density motor, or an excessively high torque density motor.

The first joint actuator 105 may be a quasi-direct drive actuator, having a gear ratio of about 24:1, and in some embodiments, may have a gear ratio of about 22:1. Accordingly, the first transmission 115 may be a very low ratio transmission and may include a planetary gear system such as shown in FIG. 5 and described hereinbelow. The first transmission 115, in other embodiments, may be a low-ratio transmission, an extremely low-ratio transmission, or an excessively low-ratio transmission is a transmission.

The second joint actuator 160 includes at least a second motor 165 and a second transmission 170. The second motor 165 and second transmission 170, in this embodiment, may be positioned co-axially within a second housing 175. The second joint actuator 160 may, in some embodiment, include a motor driver (not shown in the drawings) and an encoder 177 positioned in or about the second housing 175. In some embodiments, the second joint actuator 160 includes a link system 180 connecting the second joint actuator 160 with a plate 185. In some embodiments, the plate may be a prosthetic foot member. As shown in FIG. 1B, the plate 185 may be positioned within a synthetic joint covering, such as foot covering which may be placed in a shoe 187. In some embodiments, there may be a multi-axis load cell 190 coupled with the plate 185, wherein the multi-axis load cell 190 may be a 6-axis load cell for sensing at least the x, y, and z axis loads on the plate 185.

The second motor 165 in some embodiments may be a high output torque motor as described above. In other embodiments, the second motor 165 may be a very high output torque motor, an extremely high output torque motor, or an excessively high output torque motor. Similarly, the second motor 165, in some embodiments, may be a high torque density motor, a very high torque density motor, an extremely high torque density motor, or an excessively high torque density motor.

The second joint actuator 160 may be a quasi-direct drive actuator, having a gear ratio of about 24:1, and in some embodiments, may have a gear ratio of about 22:1. Accordingly, the second transmission 170 may be a very low ratio transmission and may include a planetary gear system such as shown in FIG. 5 and described hereinbelow. The second transmission 170, in other embodiments, may be a low-ratio transmission, an extremely low-ratio transmission, or an excessively low-ratio transmission is a transmission.

The combination of at least a high output torque motor and at least a low-ratio transmission may enable at least one or both of the first joint actuator 105 and the second joint actuator 160 to be backdrivable. A prosthesis may be backdrivable if the user or environment can drive their joints without a high resistive torque from the prosthesis. The backdrivability of at least one of the first joint actuator 105 and second joint actuator 160 may enable the prosthesis to use less power from the power source 195. In this embodiment, the first joint actuator 105 and second joint actuator 160 may also be configured such that when one of the first joint actuator 105 or second joint actuator 160 is drawing power from the power source, the other of the first joint actuator 105 or second joint actuator 160 may be generating power for the power source 195.

In some embodiments of the prosthesis 100, may include one or more dampers, such as a clutch, which in some embodiments may be a magnetic clutch, or other damping mechanisms on each of the first joint actuator 105 and second joint actuator 160 to dampen movement of each joint actuator.

Figure 2A:
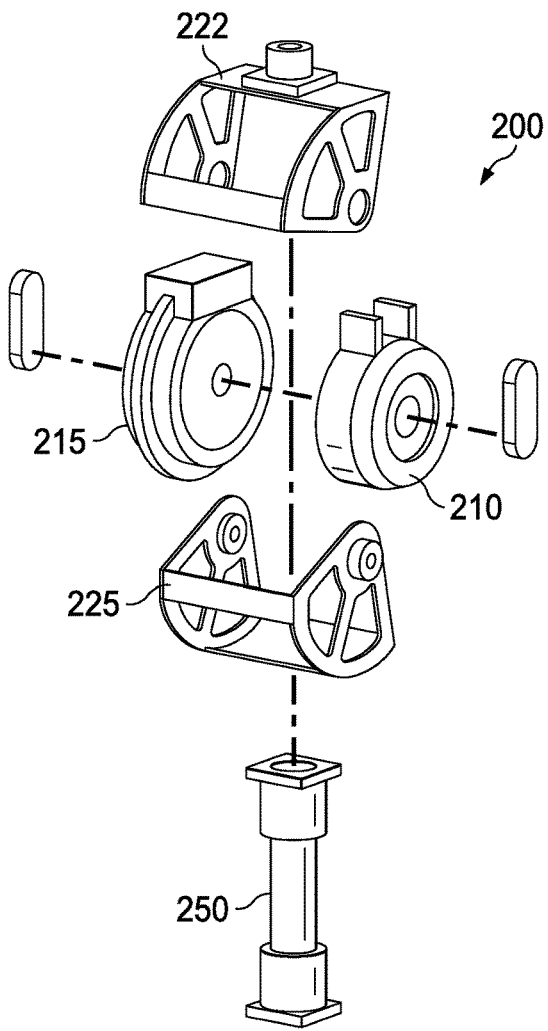
FIGS. 2A and 2B are an exploded and assembled view of one embodiment of a first joint actuator which may be used in embodiments of a powered prosthesis according to the disclosure.
Figure 2B:
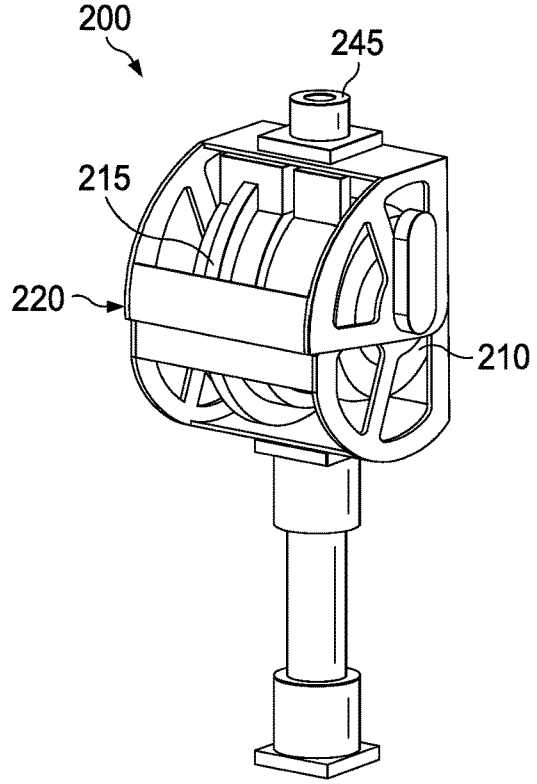

Referring now to FIGS. 2A and 2B, there is shown an exploded and assembled view of one embodiment of a first joint actuator 200 according to the present disclosure, shown and described as a knee joint. The first joint actuator 200 may be constructed similar to and have similar components and features of first joint actuator 105 shown in FIGS. 1A and 1B and described above. Although the physiological knee is a polycentric joint, it is often modeled as a single axis joint due to the minimal benefit gained from such an increase in design complexity. Therefore, the first joint actuator 200 shown in FIGS. 2A and 2B is designed as a simple hinge, which includes an upper hinge piece 222 and lower hinge piece 225, which together comprise a first housing 220. In this embodiment, the upper hinge 222 attaches to a socket on the user's residual limb via an adapter 245, such as a pyramid adapter. The lower hinge 225 may be rigidly attached to the gearbox output, thus acting as the joint actuator output. Components of the joint actuator 200, such as a first motor 210 and a first transmission 215, may be attached to the upper hinge 222, instead of the lower hinge 225, to minimize cable movement during gait. This design may keep the first motor 210 and first transmission 215 coaxial within the first housing 220, which avoids the need for additional material/components to transfer motion from the motor axis to the first joint actuator 200.

This first joint actuator 200 is designed to allow simple changes to adjustable components so that the prosthesis may be configured for different use cases (i.e., modified range of motion and shank length). This may be accomplished using swappable hard stops and modular actuators separated by a pylon. Knee motion may be constrained, in some embodiments, by bumpers may be 3D printed using a compliant material, such as TangoPlus, Stratasys, Minn., USA (in the example), to dampen the impact of the upper hinge 222 and lower hinge 225 at maximum flexion and extension. Interchangeable bumpers of varying thickness allow the first joint actuator 200 to be configured with desired limits to knee flexion and extension. With no bumpers in place, the first joint actuator's 200 range of motion includes about 112° flexion and about 5° hyperextension.

Connected to the bottom of the lower hinge 225 is an adjustable pylon system 250. The pylon system 250 system includes, in one embodiment, a universal prosthetic pylon held by two tube clamps. Each tube clamp uses a single bolt to apply pressure around the circumference of the pylon, thus holding it in place. Due to this design, the distance between the first joint actuator 200 and a second joint actuator may be continuously adjusted for users with heights ranging from at least about 1.52 m to at least about 1.98 m (5' to 6'6"), which can accommodate approximately 99.5 and 91.8 percent of all males and females, respectively. The pylon system 250 may also be rotated by a prosthetist to properly align the abduction/adduction of a prosthetic leg's second joint actuator, such as an ankle actuator.

Referring now to FIGS. 3A and 3B, there is shown an exploded and assembled view of an embodiment of a second joint actuator 300 according to the disclosure. The second joint actuator 300 may be constructed similar to and have similar components and features of second joint actuator 160 shown in FIGS. 1A and 1B and described above. Similar to the first joint actuator 200, second joint actuator 300 is designed with a single axis of rotation to simulate, for example, an ankle joint. Although the concept and capabilities of the two joint actuators are the same (i.e., torque and velocities), the physical layout of the second joint actuator 300 may be different from that of the first joint actuator 200. At the first joint (such as a knee), the axis of rotation of the motor and the joint output are, in some embodiments, coaxial. At the second joint actuator 300, such as an ankle, the motor axis of rotation is moved proximal to the body for two main reasons: users expend more metabolic energy wearing a mass that is more distal on the body, and overall joint actuator width would not allow the prosthetic foot to wear a cosmetic foot shell or shoe. The second joint actuator 300 includes at least a second motor 365 and a second transmission 370, which in some embodiments, may be positioned co-axially within a second housing 375. With the second motor 365 and second transmission 370 moved proximal to the body of a user, a parallelogram 4-bar linkage mechanism 380 may be implemented to translate the torque from the output of the gearbox distal to the location of the anatomical ankle joint. Other powered prosthetic ankles may have utilized linkage mechanisms to alter joint torque or align impact loads, the linkage mechanism 380 of the second joint actuator 300 may be used to reduce metabolic energy expenditure and to satisfy size constraints. The second joint actuator 300 may be mechanically constrained by hard stops located at approximately 45°, which provides ample rotation for a wide range of tasks, while preventing any harm to the user or system due to excessive ankle flexion. A load cell 390, such as a 6-axis load cell, may be mounted below the second housing 375. Further, an off-the-shelf Ottobock LoRider prosthetic foot may be attached to the bottom of the load cell 380. The low profile of this foot in conjunction with the layout of the second joint actuator 300 allows an ample amount of room for a cosmetic foot shell to be installed, allowing the user to wear most styles of shoes.

Referring now to FIGS. 4A-4C, there are shown tables and a graph illustrating power requirements and component weights for one embodiment of a prosthesis according to the disclosure derived according to the parameters and process discussed herein. FIG. 4C presents the needed power throughout the gait cycle, including the power required by the electronics system. Structural components of both the first and second joint actuators were optimized using the finite element analysis software, ANSYS (in this example), to ensure structural integrity against impact and loading conditions of a 113.4 kg (250 lbs.) user during level ground walking and stair ambulation. Most machined components may be constructed using metals, including but not limited to aluminum and stainless steel, such as 7075-T6 aluminum, with a few shafts, gears, and bearings made of stainless steel. One embodiment of the prosthesis 100 weighs approximately 6.05 kg. In an effort to reduce weight, components that are under minimal loading conditions may be 3D printed in ABS plastic. This weight does not include the leg's Lithium-Polymer batteries, TP16004SA80X, Thunder Power, Nevada, USA, since they are kept off-board and are subject to change when mounted onto the leg. (In this example, due to the potential for high regenerative currents flowing to the batteries, the batteries were kept off-board until an active battery management system can be implemented.) The first joint (knee) actuator is approximately 13.72 cm wide (mediallateral) by 12.95 cm deep (anterior-posterior). The second (ankle) joint actuator is approximately 6.50 cm wide by 7.66 cm deep. The section corresponding to the calf is approximately 11.88 cm wide by 12.91 cm deep, which equates to approximately the 50th percentile of adult male and female calf circumference. Lastly, in an effort to reduce weight, components that are under minimal loading conditions were 3D printed in ABS plastic. The prosthesis in one embodiment was powered using a DC power supply (N8736, Keysight Technologies, California, USA in the example test), but other embodiments may be battery powered.

High-torque motors typically used in industrial settings have large masses and volumes due to their robust housings and heat sinks. In addition, these motors are typically fixed in place, leading to minimal consideration of weight in their design. However, for implementation into a powered prosthetic leg, a motor with high torque density may be selected to ensure that the first and second joint actuators could produce the required torque while remaining as light as possible. To this end, an ILM 85×26 motor kit (Robodrive, Germany in the example) was selected. This frameless, brushless DC motor kit allowed for the design of a custom housing that can withstand loading conditions and dissipate heat, while reducing the weight compared to industrial motor assemblies. This motor has a manufacturer rated torque of 2.6 Nm, peak/stall torque of 8.3 Nm, and velocity up to 1500 rpm. Additionally, it is rated at 410 W, 48 V, and 11 A. The motor is driven by a 25/100 Solo Gold Twitter motor driver (Elmo Motion Control, Petah Tikva, Israel in the example), which has a rated current of 17.6 A and a peak current of 35.2 A. Additionally, the driver's mass of 22.2 g, in this example, is ideal for minimizing overall actuator mass.

Referring now to FIGS. 5A and 5B, there is shown an exploded (5A) and assembled (5B) view of embodiment of a gear system 500 that may be used in a transmission of either the first transmission or second transmission such as first transmission 115 and second transmission 170. In order to increase the torque and reduce the speed of the motor to fit within the desired torque/velocity range, a custom single-stage stepped-planet compound planetary gear transmission (SPC-PGT) with a 22:1 gear reduction may be used. The gear system 500, in this embodiment, SPC-PGT includes at least sun gear 505, at least one ring gear 510, and six planet gears 515 and 520 such as gears procured from SDP/SI in New York, USA (in the example). Traditional planetary gear transmissions have only three planet gears, which mesh between the sun gear 505 and ring gear 510. However, the SPC-PGT shown in FIG. 5 includes for three sun-planet gears and three ring-planet gears. Each sun-planet gear may be coaxially fixed in relation to its corresponding ring-planet gear through a keyed shaft. The sun-planet gears 515 may mesh with the sun gear 505, radially located, in some embodiments, about 120° apart from each other. Similarly, the ring-planet gears 520 may be meshed with the ring gear 510, and may also be radially located about 120° apart from each other. The shafts of the planet gears 515 and 520 may be held on either side by what is commonly referred to as a planet carrier 525.

Although planetary gear transmissions have multiple input-to-output configurations, the presented gearbox uses the sun gear as the input and the planetary carrier as the output to achieve the maximum ratio possible given a specific gear set. A traditional single-stage planetary gear transmission with the same input to output configuration has a reduction ratio found by $\tau_m/\tau_j=(D_r+D_s)/(D_s)$, whereas the reduction ratio of the single-stage SPC-PGT is found by $\tau_m/\tau_j=1+(D_rD_{sp})/(D_sD_{rp})$, where $\tau_m$ and $\tau_j$ are the motor and joint torque, respectively, and $D_s$, $D_{sp}$, $D_{rp}$, and $D_r$ are the sun, sun-planet, ring-planet, and ring gear diameter, respectively. Due to geometric constraints of a traditional planetary gear transmission, reduction ratios are typically limited to 10:1. However, the SPC-PGT as shown in FIG. 5 may easily achieve higher reduction ratios in the same geometric volume. Although the presented embodiment differs from a traditional single-stage planetary gear transmission, the number of gears meshed together is the exact same, thus increasing the obtainable reduction ratio while maintaining efficiency. Coupled to at least a high output torque motor, this transmission provides a continuous torque of 57.2 Nm and a peak torque of 182.6 Nm, demonstrating a larger scale application of a SPC-PGT transmission compared to a jumping robot.

Referring now to FIG. 6, there is shown a block diagram of one embodiment of an electrical system that may be used with prosthesis 100. Sensor feedback is critical for both the control and safety features of the device. Each joint actuator may have at least one encoder, such as Optical Quadrature Encoder with 4096 cycles per revolution, US Digital, Washington, USA. Fixed to a shaft of the motor, the encoder sends motor position data to the motor driver and system controller. Once at the controller, this data is multiplied by the transmission reduction ratio for position and velocity feedback. Although only one encoder was used per joint actuator, some embodiments of the prosthesis may include a second encoder which may be used at each joint actuator output, allowing direct joint measurements for position and velocity feedback. For this reason, some embodiments may include two encoders per joint actuator. Additionally, both motors may contain two thermistors, such as Pt1000 thermistors embedded in the stator. The thermistors monitor the internal temperature of the stator to ensure that the motor is not damaged during use. In some embodiments, the second joint actuator may include a 6-axis load cell, such as A M3564F 6-axis load cell, Sunrise Instruments, Nanning, China (in the example). The 6-axis load cell may be located below the axis of the second joint, such as the ankle joint axis, and provide force and moment information usable for ground detection and reaction forces during gait. The 6-axis load cell is capable of reading 2500 N/200 Nm along the x and y axes and 5000 N/100 Nm along the z axis. These sensors interface with the system's microcontroller, which in some embodiments, may be a myRIO, National Instruments, Texas, USA. Some embodiments of the controller presented herein may be implemented in the National Instruments LabVIEW software environment and then imported onto the myRIO. Embodiments of the prosthesis may use the Control system shown and described in U.S. patent application Ser. No. 15/550,556, entitled "Systems and Methods for Prosthetic Control," filed on Aug. 11, 2017, commonly assigned with this application and incorporated herein by reference.

Referring now to FIGS. 7A and 7B, there are shown features illustrating how low-inertia design of the joint actuators may facilitate smooth and easy switching between position and impedance control paradigms, wherein this characteristic can be leveraged for design of a walking controller.

Due to its inherent simplicity and robustness, a PD controller is the most common choice for the joint position control of robotic systems:

$$\tau_m = K_p(\theta_d - \theta) + K_d(\dot{\theta}_d - \dot{\theta}) \tag{1}$$

where Kp and Kd are positive PD gains and θd and θ are the desired and actual positions, respectively. Since the PD gains determine the pole's frequencies of the closed-loop system, these gains are set as high as possible to minimize tracking error and phase lag. In applications such as prosthetic legs, controllers that rely on a kinematic phase variable generally utilize this approach.

An alternative approach which may be commonly used in control of a powered prosthesis is impedance control. The most common way to perform joint impedance control is using joint torque feedback to produce the desired behavior. Note that for a fixed transmission ratio n the general relationship between motor commanded torque τm and joint torque τj can be written as the following formula:

$$\tau_j = \tau_m + n^2 I_m \ddot{\theta} + n^2 b_m \dot{\theta} + f(\theta, \dot{\theta}, t) \tag{2}$$

where $I_m$ and $b_m$ are motor inertia and damping, respectively, θ is the joint angle, and f contains nonlinear and time-dependent losses such as Coulomb friction, stiction and hysteresis. Note that $\tau_m = nk_t i_m$, where $k_t$ is the motor's torque constant and $i_m$ is its current, commanded to the driver. Torque feedback is necessary to decrease the effect of unmodeled dynamics (f) and common uncertainties of inertia and damping parameters in (2). However, an actuator designed with minimal unmodeled dynamics can be utilized to reliably simulate any desired dynamics (an arbitrary impedance, for instance) without requiring a torque sensor feedback. This is especially important in a control problem such as walking, where unexpected interactions with the environment (impacts) are always likely to occur. The high noise and limited speed of closed-loop force control during walking strongly motivates the natural dynamics achievable through low-impedance actuation. With an ideal actuator, a PD controller can be considered an open-loop impedance controller, with proportional and derivative gains acting as stiffness and damping. Based on this, we expect that changing the stiffness and damping coefficients in Eq. (1) will enable a wide range of dynamic behaviors through highly variable joint impedances. Furthermore, without any change in the control structure aside from increasing the gains, the controller may effectively work as a position control scheme.

A previous embodiment of a powered prosthesis used a walking controller for the powered knee-ankle prosthesis based on a Finite State Machine (FSM). For each state of the FSM, they used an impedance controller of the form of the following equation:

$$\tau_m = K_p(\theta_d - \theta) - K_d \dot{\theta} + K_2(\theta_d - \theta)^3, \tag{3}$$

where Kp, Kd, and K2 are tunable constant values for each state. The form of the impedance controller (3) was chosen to fit human joint torque profiles. However, due to high impedance of the actuators, the final values of the tuned parameters were quite different from biological values. This implies that the total joint impedance is different from the commanded impedance due to the non-negligible actuator impedance. The small correlation between the tuned and reference values of these parameters often requires lengthy sessions of tuning for each set of parameters to achieve the desired performance, since they are not known beforehand and change from one subject to another.

FIG. 7A depicts the FSM designed to control one embodiment a prosthesis according to the disclosure. Impedance controllers have been used for control of early and mid-stance. This was motivated by the fact that impedance control provides reliable and smooth interaction with the environment (i.e., the ground). Since there is no interaction with the environment during swing phase, a time-based position tracking controller was designed based on able-bodied reference trajectories. Time-based position tracking may provide a stronger pushoff and a smoother transition to swing phase. This is perhaps due to the fact that impedance control is essentially a reactive strategy (reacting to contact with the environment), whereas pushoff is an active process that provides the main source of (positive) energy in gait. Based on this, time t is set to zero when the transition to pushoff takes place. The duration of pushoff, swing, and touchdown subphases are determined by the preset speed-dependent parameters tpo, tsw, and ttd. At the start of each subphase, the change of parameters (Kp and Kd, and also θd for impedance-based subphases) is performed through the use of a third-order spline, to avoid any discontinuity in the commanded torque.

Note that an important feature of the controller used with embodiments of the prosthesis according to the disclosure is that the controller does not require ground contact sensing. In particular, the purpose of the touchdown subphase is to change the PD parameters for smooth transition to the impedance control of the early stance subphase. In this way, as the first joint actuator (knee) extends, the controller "expects" the ground contact rather than sensing and then reacting to it. Thereby, the reaction to impact becomes a part of the natural (open-loop) dynamics of the system. This type of natural response is also observed in biological locomotion and used in legged robot applications. Based on this, unlike all other subphases in which Kp and Kd are constant values (apart from the short smoothing period at the start of each subphase), gains are gradually changed throughout the touchdown subphase to match those of early stance.

The default stiffness values (equivalent to Kp, as discussed) for the impedance control subphases were picked from the quasi-stiffness of able-bodied subjects. A small damping coefficient (Kd) was added to obtain a smoother operation. The details of the walking experiments and the selected gains are presented below.

Referring now to FIG. 8 there are shown views and results of testing experiments to quantify backdrive torque and free-swing capabilities of first and second joint actuators of embodiments of prostheses according to the disclosure. The testing experiment described herein aims to quantify the backdrive torque of the first and second joint actuators, i.e., the torque required at the output of a joint actuator to rotate the motor through its transmission.

Figure 8A:
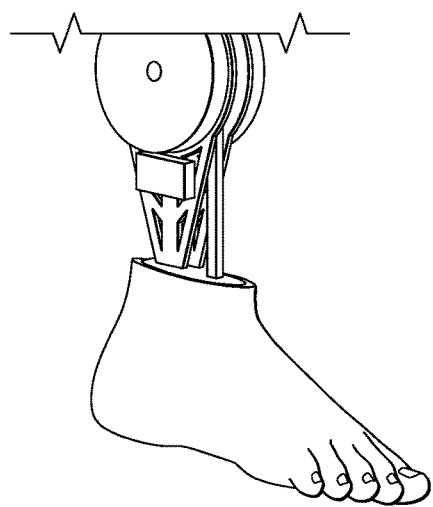

Referring to FIG. 8A, for this experiment, the second joint (ankle) actuator was rigidly fixed to the benchtop setup with motion still being allowed at the ankle joint. A force was then applied with one finger to the toe of the foot. The applied force gradually increased until the joint moved. A total of nine trials of this experiment were conducted, three each with the ankle initially positioned at 200, 00, and 20°. For the case of 0° and 20°, a downward force was applied to result in plantar flexion. For the case of −20°, an upward force was applied to result in dorsiflexion.

Throughout this experiment torque data was collected from the 6-axis load cell. Torque maxima for each trial were extracted from the collected data and averaged for each initial starting position. These maxima occurred directly before the applied torque overcame static friction within the system. The magnitudes of the mean peak torque values were 3.41 Nm, 3.23 Nm, and 3.22 Nm for the initial ankle position of −20°, 0°, and 20°, respectively. The tests confirmed the actuator's ability to be backdriven with a low amount of torque.

Figure 8B:
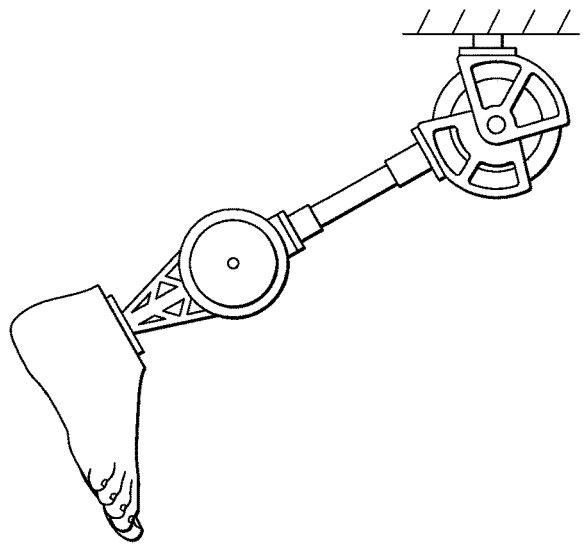
Figure 8C:
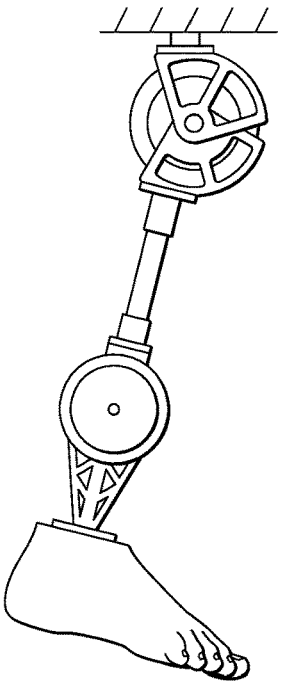
Figure 8D:
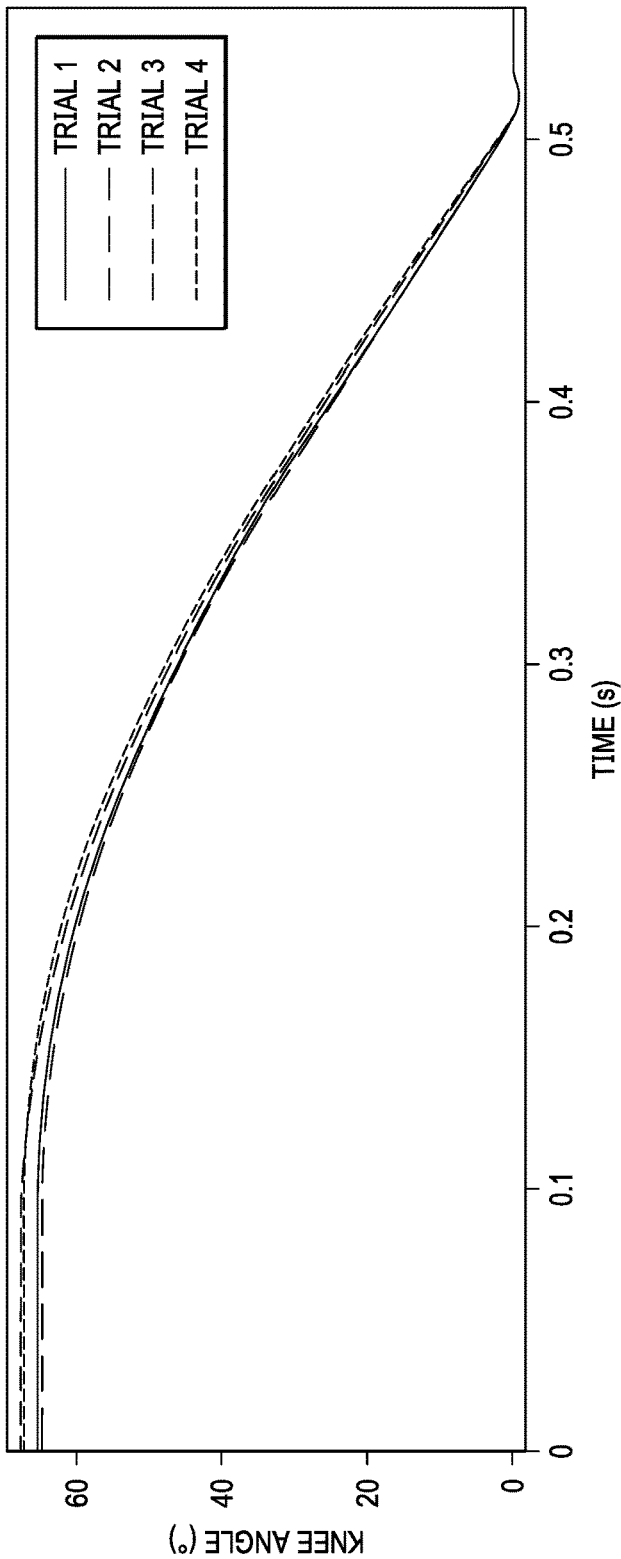

Referring now to FIGS. 8B-8D, there are shown test results from a free-swinging knee test performed using one embodiment of a prosthetic according to the disclosure. A free-swinging knee has the benefit of simplifying control effort during swing phase, therefore leading to a more energy efficient system. A simple experiment was performed to show that the knee could be backdriven by the weight of the shank (such as adjustable connector 150) and foot alone, thus simulating the swing phase of gait. With the motors unpowered, four trials were performed in which the top of the knee was fixed to the benchtop setup, flexed between 65° and 70°, and then released without a push. The experimental setup can be seen in FIGS. 8B and 8C. FIG. 8D shows the knee position for each of the four trials from the point of release until it reached the mechanical hard stop. With knee flexion peaking at approximately 70° for level walking, as shown in FIG. 8D, that the knee may exhibit free-swing capabilities since the knee repeatedly returns to zero after being released from a specified height.

It should be noted that the missing dynamics of walking were not included in the tests or results shown in FIGS. 8B-8D, such as hip moment and ankle push off, should decrease the free swing timing. In addition, the control strategy for walking may accelerate the free swinging knee motion.

A free-swinging knee has the benefit of simplifying control effort during swing phase, therefore leading to a more energy-efficient system. Toward this end, a simple experiment was performed to show that the knee could be backdriven by the weight of the shank and foot alone, thus simulating the swing phase of gait. With the motors unpowered, four trials were performed in which the top of the knee was fixed to the benchtop setup, flexed between 65° and 70°, and then released without a push. This experimental setup can be seen in FIGS. 8B-8D. FIG. 9 shows the knee position for each of the four trials from the point of release until it reached the mechanical hard stop. With knee flexion peaking at approximately 70° for level walking, it can be seen in FIG. 9 that the knee exhibits free swing capabilities, since the knee repeatedly returns to zero after being released from heights common during walking.

Referring now to FIG. 10, there is shown test results identifying the parameters that contribute to its impedance, such as inertia and damping. To identify such parameters, open-loop velocity bandwidth tests were performed. During these tests the first joint (knee) actuator was fixed on a benchtop setup with the mechanical output disconnected to ensure continuous rotation was not limited by the mechanical hard-stops. The experiment was performed from a very low frequency up to the point that the test was halted due to excessive shaking and vibrations, i.e., 0.1 to 35 Hz. The resulting magnitudes presented in FIG. 10 shows a DC offset of 7.6 dB and a cut-off frequency of 6 rad/sec at 4.6 dB (or −3 dB from DC offset). Using these values, with the assumption that the system is a first-order system, the following transfer function is used to determine the inertia, I=0.0696 kg·m², and damping, b=0.4169 Nms/rad.

$$G(s) = \frac{1}{Is + b} \quad (4)$$

To verify, these parameters were used in the matlab function bode to plot the transfer function in Equation (4) over the experimental data shown in FIG. 10. The strong agreement between the magnitude from experimental data and from the calculated inertia and damping terms confirms the correctness of these parameters.

Real-world physical systems generally act as low-pass filters, attenuating high frequency inputs. In the case of actuators, especially electric ones, the cut-off frequency of the system becomes an important factor in characterizing the speed by which the output can be actively controlled through changing the input signal. Since closed-loop position controllers are commonly implemented in powered prostheses, closed-loop position bandwidth tests were conducted to characterize the maximum frequency that the low-impedance actuators presented in the disclosure may achieve.

During these tests the first joint (knee) actuator was fixed on a benchtop setup with the mechanical output disconnected to ensure continuous rotation was not limited by the mechanical hard-stops. The experiment was performed from a very low frequency up to the point that the test was halted due to excessive shaking and vibrations. The experiment was conducted with an input sine wave with three separate amplitudes, 5°, 10°, and 15°. The results, shown in FIG. 10, indicate cut-off frequencies of 67.4, 90.1, and 134.0 rad/s for the 5°, 10°, and 15° amplitude, respectively. Noting that a frequency analysis of human gait shows that the highest frequency content of walking is in the range of ~6-22 rad/s, the actuator is expected to be completely capable of tracking the human-like joint trajectories.

Referring now to FIG. 11, there are shown position tracking of normative gait trajectories as various frequencies. FIGS. A, C, and E present ankle tracking at 0.5, 1.0, and 1.3 Hz respectively. FIGS. B, D, and F present knee tracking at 0.5, 1.0, and 1.3 Hz respectively. Many legged locomotion control paradigms, for instance those originating from Hybrid Zero Dynamics (HZD), rely on stiff and precise position control of the joints. To examine the actuators' position tracking capabilities, a proportional-derivative (PD) controller with a gravity compensation term was implemented for each actuator. For this experiment, both joint actuators were assembled together and the complete prosthesis was mounted onto the benchtop setup, as in FIGS. 8B and 8C. The normative joint trajectories were tracked at frequencies of 0.5 (slow walking), 1.0 (fast walking), and 1.3 Hz (running). FIG. 12 displays the tracking performance per joint for the frequencies mentioned.

FIGS. 12A-D display tracking performance per joint for the increasing frequencies. For all three frequencies the second joint (ankle) actuator is able to track the position with little error (max 0.27°, 0.45°, and 0.55° for 0.5, 1.0, and 1.3 Hz respectively). Although the first joint actuator (knee) tracking errors are relatively small for 0.5 and 1 Hz (max 1.04° and 6.42° respectively), at 1.3 Hz the difference between desired and actual trajectories starts to become visible (max 13.17°). This error is mainly due to phase lag between desired and measured trajectories. Neglecting this phase lag reduces the maximum knee tracking error to 2.05° and 4.56° for 1.0 and 1.3 Hz, respectively. The higher error in the knee angle is due both to larger mass and inertia acting against the knee actuator as well as the larger range of motion and higher acceleration of the knee joint, compared to the ankle. It should also be noted that joint torque was saturated to 120 Nm for safety during these tests, which could be relaxed in the future to reduce this error. Moreover, walking with the prosthesis will provide an aiding hip moment that could improve these results. Therefore, the prosthesis may be completely capable of supporting position-based control paradigms for the full range of walking speeds and some running speeds.

Note that as the frequency increases, the first visible discrepancy between desired and actual trajectories appears at the knee flexion and extension immediately after the touchdown phase, which is the most difficult part of the cycle for the actuator to follow. In this region of gait, active position tracking is not strictly required because the function of the knee is to absorb energy during weight acceptance with the ground. Different control paradigms (not based on position control) can take advantage of the actuator design to control this part of the gait more effectively, and as a result, can potentially achieve even higher frequencies.

The previous sets of experiments showed that the special design of the actuators and its high bandwidth makes it capable of supporting walking control paradigms designed based on precise joint position tracking. Experiments shown and described herein show that the joint actuator design also works well for compliant walking control paradigms. This especially becomes important when one considers the most difficult part of the human joint trajectories to be mimicked by position control, namely the quick flexion and extension of the knee immediately after impact FIG. 11F. This happens in humans due to natural compliance of the knee joint, rather than precisely following a prescribed position trajectory. This motivates further testing of the ability of the designed actuator for specified impedance behaviors.

Referring now to FIGS. 12A-D, there is shown open-loop impedance of the ankle joint with various $K_p$ and $K_d$ gains, which depicts the resulting ankle torques of four different experimental cases. Solid and dotted lines correspond to commanded and measured torque respectively. Reduced PD gains used are as follows per the following FIGS.: 12A $K_p=0$ and $K_d=0.5$; 12B $K_p=0.8$ and $K_d=0.05$; 12C $K_p=0.8$ and $K_d=0.05$; and 12D $K_p=3$ and $K_d=0.15$. The first and second case, FIGS. 12A and 12B show pure stiffness and pure damping tests, respectively, whereas cases three and four, shown in FIGS. 12C and 12D depict a combined stiffness-damping control. As FIGS. 12A-D show, there is a very good agreement between measured joint torque and commanded motor torque in the first three cases, proving that the effect of unmodeled dynamics is negligible for torques over ~10-20 Nm. Note that this is much smaller than joint torques during stance phase, making the joint actuator completely suitable for any kind of compliant control during stance. To investigate the limitation of the control for low torques (where the effect of unmodeled dynamics becomes considerable), small torque was applied to the end-effector which shows a noticeable difference between the two torques for amplitudes less than about 5 Nm as shown in FIG. 12D. The difference between torques is around the value obtained for the backdriving torque as presented before (about 3 Nm).

Walking experiments were conducted to assess the performance of the powered prosthetic leg under the loading conditions for which it was designed. Using the proposed controller, a 73 kg, 1.76 m tall, able-bodied subject walked on the leg at different speeds on a treadmill, as shown in FIG. 13. Since the subject was able-bodied, the prosthetic leg was attached to a custom bypass adapter. The subject wore a shoe lift on the non-prosthetic leg to equalize their leg length to that of the prosthetic leg. While walking on the treadmill, the subject wore a safety harness around their torso to prevent injury in the case of tripping or falling. An emergency stop button, which would disable the motors when pushed, was given to the subject if they felt the need to stop at any time.

The subject was asked to walk on the treadmill for approximately 60 seconds at a range of walking speeds (0.9, 1.1, 1.3, and 1.6 m/s), while wearing the prosthetic leg. In order to follow the speed-independent results, Kp and Kd values corresponding to impedance control states were held constant across speeds. Also testing found that the effect of swing-phase PD gains across different speeds was negligible and these value were also held as constant. Only in pushoff were the ankle gains tuned until the subject felt a comfortable propulsion force. Tables III and IV summarize the parameters used for these trials.

During these experiments, gait kinematics and kinetics were collected for validation of the prosthetic leg. Disregarding gait acceleration and deceleration at the beginning and end of the walking trial, 30 seconds of continuous walking was captured for each speed. The data was divided through detection of ground impact using the ankle load-cell, which in turn allows the calculation of gait statistics, such as means and standard deviations. To further study the effect of the leg's actuator design during gait, two other measurements were recorded: power drawn from the battery and acoustic sound levels.

Once the parameters were tuned for the walking speed, the able-bodied subject walked on the treadmill with the prosthesis. FIG. 14A shows the collected knee and ankle joint angles for different walking speeds and compares them to normative gait kinematics. The able-bodied dataset does not include high speed gaits for inclusion in FIG. 15D. The gait cycle begins and ends at ground impact, with the transition from stance to swing occurring around about 60% of the gait cycle subject walked on a treadmill.

FIGS. 16 and 17 depict the commanded versus measured torques of the knee and ankle joints, respectively, during walking experiments. Contrary to the mean and standard deviation presented in FIG. 15, these two figures present several consecutive steps. This is to better show how accurately the desired torque be can realized through open-loop control. As expected from the results of the benchtop tests, the two torques closely match, confirming the hypothesis regarding low actuator impedance and unmodeled dynamics.

These biomechanical results demonstrate that the presented prosthetic leg can indeed perform as intended across walking speeds.

One benefit of using low-impedance joint actuator may be similar to that of series elastic actuators (SEAs). Although the joint actuators implemented in the presented prosthesis do not have an elastic element, they do have the ability to store energy. This energy storage occurs in the phases of gait when negative work is being done on one embodiment of the prosthesis, such as prosthesis 100. When this occurs, the generated energy can either be used within the leg's electrical system or to recharge the leg's batteries. This reduction of power consumption may increase the efficiency of the prosthesis 100 for an extended battery life.

To evaluate the electrical power consumption and regenerative capabilities of the leg, a current probe (TCPA300, Textronix, Oregon, USA, in this example) was used to measure real-time current flowing to and from the entire leg. In addition, the battery's voltage was also recorded. These signals were measured by an offboard oscilliscope (DPO 2024B, Textronix, Oregon, USA in this example) and saved to an off-board computer. The combination of these two signals allows for the calculation of the prosthetic leg's total or consumed electrical power at each instant, P=iv, where i is the current, and v is the voltage. This power is indicated in FIG. 18 by $P_{Total:iv}$, where Total indicates the inclusion of power at both joints, and iv indicates that it is based upon measured current and voltage. This power is compared against the leg's total output mechanical power, calculated using $P_{Total:\tau\omega}$=τknee·ωknee+τankle·ωankle, where τω indicates that the power is based upon measured torque, τ, and measured velocity, ω. Additionally, knee power (PKnee:τω) and ankle power (PAnkle:τω) are presented. By integrating these curves, electrical and mechanical energies are calculated and presented in Table V. Positive values indicate produced energy, whereas negative values indicate regenerated energy. The total mechanical energy is given by Emech=$EP_K$+$ER_K$+$EP_A$+$ER_A$, where $EP_K$, $ER_K$, $ER_K$, and $ER_K$ indicate produced knee, regenerated knee, produced ankle, and regenerated ankle energies, respectively. The total efficiency of the prosthesis is defined as η=Emech/Ebatt, where Ebatt is the total electrical energy provided from the battery. Note that as speed increases, efficiency also increases. One contributing factor to this is the 20 W consumed by the electronics and on-board computer, which has more influence on the efficiency relative to mechanical power during slow walking. Moreover, at slower walking speeds, the motors provide torques at lower velocities, where the electric motor is less efficient due to winding losses.

As expected, the results shown in FIGS. A-D illustrate that in regions of gait where rapid deceleration and joint damping typically occurs, the joint actuator may use negative power and therefore regenerate energy and supply power to the power source. Energy is regenerated and shared between joint actuators when one joint actuator regenerates energy while the other joint actuator is consuming it. This is shown in the results illustrated in FIGS. 18A and 18B between approximately 40% and 55% of the gait cycle, where the ankle mechanical power is negative while knee power is positive. Alternatively, regenerated energy returns to the battery when a joint regenerates more power than is required by the other joint or the leg's electrical system. As shown in FIGS. 18A-D, between approximately 75% and 95% of the gait cycle, when the first joint (knee) actuator regenerates energy and the second joint (ankle) actuator does not. Both energy sharing and regeneration aid in reducing the average energy consumed per gait cycle. One embodiment of the prosthesis according to the disclosure may average about 0.81, 0.83, 0.93, and 1.39 W/kg (normalized by the subject's mas) for 0.9, 1.1, 1.3, and 1.6 m/s, respectively. With the selected batteries, the prosthesis may currently operate for 1.29, 1.26, 1.13, and 0.76 hours of continuous walking or 2520, 2774, 2710, and 2159 prosthetic steps at 0.9, 1.1, 1.3, and 1.6 m/s, respectively. Note that the total step count for the user would double when considering the intact limb. The active time and step count can be increased by incorporating higher capacity batteries, at the cost of additional mass.

To investigate the reduction of the acoustic sound level of the presented powered prosthetic leg, a sound level meter (PCE-322A sound level meter, PCE Instruments, Florida, USA, in this example) recorded the magnitude of the sound coming from the leg during the walking trials. The sound meter was placed at the height of the user's ear, approximately 1.5 m away, to measure the magnitude of the sound heard from their perspective. FIGS. 20A and 20B compares the sound level of the presented prosthetic leg to a previously published leg that utilizes high-speed, low-torque motors with high-ratio transmissions. Note that the y-axis scale (dBA) is not linear, but logarithmic. In this figure, the gait cycle begins and ends at ground impact, with the transition from stance to swing occurring at about 60% of the gait cycle. Due to the low sampling rate of the sound level meter (10 Hz), large changes in sound level readings may look like instantaneous jumps in data, which explains why the values at 0% and 100% do not align. In fact, peaks seen in the new joint actuator's sound level at the beginning of the gait cycle actually originate from impact with the ground, instead of the leg's actuators. Since control of foot planting is reduced when walking with a prosthetic leg, which continues to decrease as speeds increase, the jump in sound is likely to be a result of the controller managing the leg at impacts, although these instantaneous jumps are generally not seen in the traditional actuation style. Additionally, the low-impedance actuation presented is much closer to the sound level of able-bodied walking. As speed increases, the ambient, able-bodied, and low-impedance leg's sound levels are generally shifted upward, which is related to the increased sound of the treadmill. In fact, the difference between able-bodied and the low-impedance actuator's sound levels are fairly similar across speeds, not considering impact with the ground. This trend is not as evident in the high-impedance leg. Therefore, since the prosthesis with low-impedance joint actuators is much quieter than a traditional prosthesis with high-impedance joint actuators, ground-impacts and ambient sound levels have a greater contribution to its total sound level.

As shown by the results in FIGS. 20A and 20B, low-impedance actuation is much quieter than traditional actuation in joint actuators. Specifically, one embodiment of a prosthesis according to the disclosure may be on average at least 7 dB and 6 dB quieter (including impacts) than that of the conventional leg at 0.9 and 1.3 m/s, respectively. If impacts were disregarded, the difference is expected to be much greater.

FIG. 21 illustrates a Table comparing inertias, transmission rations, and joint torque of joint actuators in the prostheses according to principles of the disclosure with other prosthesis. The prosthesis constructed according to the principles of the disclosure include the "Low-Impedence Leg—Knee and ankle, UTD Leg 1—Knee, and UTD Leg 1—Ankle.

Presented herein are design and experimental validation for a powered prosthetic leg with high torque density actuators. The embodiments described herein implement high torque motors coupled with low reduction transmissions. Low mechanical impedance is an inherent feature of the actuator's design, resulting in low backdrive torques to move the motor.

Experimental tests were performed to determine certain characteristics of the actuators. Due to the low mechanical impedance, the knee actuator exhibits free-swing under the weight of the leg alone. Bandwidth tests revealed the joint actuators' ability to achieve frequencies common for fast gait patterns. Closed-loop position control implemented on the leg was shown to be effective, resulting in negligible error for frequencies up to 1.3 Hz. Open-loop impedance control tests proved that the effect of unmodeled dynamics is negligible for torques over 10-20 Nm, making the actuator suitable for any kind of compliant control during stance phase of gait. The low actuator impedance and accurate impedance control make it possible to command and control the torque of the system without any torque feedback, thus allowing the removal of torque sensors from the system's design.

Testing disclosed herein illustrate that when measuring the inertia of joint actuators according to the disclosure through open-loop velocity bandwidth tests, the joint actuator inertia I was shown to be about 0.0696 km·m², which is very close to the estimated inertia given from the cad model shown in FIG. 1A, for example, which had an inertia I=0.0625 km·m². FIG. 21 presents the reflected inertias of several joint actuators in other powered prostheses. Note that in this table, values for reflected inertia only consider the motor rotor inertia, and do not include the inertias of the transmissions. This was done for consistency when comparing across joint actuators, since CAD models of other models of prostheses were not available for testing. Although the motors used in some of the prostheses constructed according to principles of disclosure had a higher rotor inertia, due to its reduced gear ratio, the reflected inertia is smaller compared to other powered prostheses; and approximately 46% smaller than some the initial design requirement discussed herein, inter alia, with respect to FIGS. 4A-4C. This was achieved while increasing available torque at the joint actuator.

A power analysis of the prosthetic leg with low-impedance actuators revealed a practical design advantage through a reduction in the average power required from the prosthesis. For level ground walking, the presented leg had an average specific power of 0.83 W/kg (normalized by the subject's mass) during normal walking speeds. This is approximately 15% lower than the 0.98 W/kg average seen in a state-of-art powered prosthetic leg and approximately 6% lower than the 0.88 W/kg average. Note that although average specific power is reduced, peak power provided (~300 W) is 50% and 20% greater than the ~200 W and ~250 W peak power. The decreased average power consumption allows the prosthesis to take between 2159 and 2774 prosthetic steps on a single charge of the power source. These values are more than sufficient for the daily use of an average transfemoral amputee, who takes approximately 1540 prosthetic steps per day. There are two main reasons for the reduced power consumption seen in embodiment of the prosthesis constructed according to the disclosure: regenerated negative power and reduced intrinsic actuator dynamics, both of which are founded in the design of the joint actuators. Negative power occurs when the user backdrives the joint actuators to create a velocity that opposes the commanded torque. This negative, or regenerated, power can either be used within the system to power the electronics of the other joint actuator, or may be sent to the power source, such as a battery. Additionally, the low gear ratio reduces the amount of friction and reflected inertia that the motors have to overcome. These design features reduce electrical power consumption while increasing peak power output compared to previous design approaches for powered prosthetic legs.

While there is not much presented in the art regarding the acoustic sound level of assistive devices such as prosthetic legs and limbs, the acoustic sound level may become more important when presenting the technology discussed herein to a consumer. The prostheses constructed according to the disclosure were shown to be on average 6 dB to 7 dB quieter than a prosthetic leg with conventional actuation. In comparison to typical household items, the sound level of the traditional high-impedance prosthetic leg is akin to a vacuum cleaner (60 dB to 70 dB at ~1.5 m), which is similar to the 70 dB (at ~1 m). However, the low-impedance prosthesis according to the disclosure is similar to a refrigerator or an electric tooth brush having a sound level of about 50 dB to 60 dB at ~1.5 m. Enclosing the prosthesis in an enclosure, insulated or not may further reduce sound levels accordingly.

Future embodiments and testing for embodiments of the powered prosthesis presented herein may include consolidating the computer, power supply, and other electronics on-board to create a self-contained prosthesis. Additional development of embodiment of the prosthesis may leverage the backdrivability of the joint actuators to implement power regeneration when negative work is being done on the leg. Such a system would aim to safely and efficiently reharvest power during these periods. Further embodiments of the prosthesis may be used as a platform for control prototyping and used in amputee experiments. Further in an attempt to reduce weight of the self-contained unit, other component designs and material selection may be optimized.

Those skilled in the art to which this application relates will appreciate that other and further additions, deletions, substitutions and modifications may be made to the described embodiments.

What is claimed is:

1. A powered prosthesis, comprising:
    a first joint actuator having a first high output torque motor having a peak output torque measured over a 10 second time period of at least about 1.0 Nm;
    a second joint actuator having a second motor;
    a connector to connect the first joint actuator with the second joint actuator; and
    a power source connected with both the first and second motors;
    wherein the first joint actuator and the second joint actuator are both backdrivable, each having a static backdrive torque of less than 10 Nm, and configured such that when one of the first or second joint actuator is drawing power from the power source, the other of the first or second joint actuator can generate power for the power source.

2. The powered prosthesis according to claim 1, further including an adapter for connecting the prosthesis with a human body and an inertial measurement unit (IMU) positioned adjacent the first joint actuator.

3. The powered prosthesis according to claim 1, further including a controller, the controller including at least a microprocessor.

4. The powered prosthesis according to claim 1, wherein the first joint actuator further includes a first housing having the first high output torque motor and a first transmission positioned co-axially therein.

5. The powered prosthesis according to claim 4, wherein the first high output torque motor is a first very high output torque motor having a peak output torque measured over a 10 second time period of at least about 1.5 Nm.

6. The powered prosthesis according to claim 4, wherein the first transmission includes a plurality of planetary gears.

7. The powered prosthesis according to claim 1, wherein the second joint actuator includes a second housing having the second motor and a second transmission positioned co-axially therein.

8. The powered prosthesis according to claim 7, wherein the second motor is a second very high output torque motor having a peak output torque measured over a 10 second time period of at least about 1.5 Nm.

9. The powered prosthesis according to claim 7, wherein the second joint actuator further includes a link system connecting the second joint actuator with a joint plate, and a 6-axis load cell coupled with the joint plate.

10. The powered prosthesis according to claim 7, wherein the second transmission includes a plurality of planetary gears.

11. The powered prosthesis according to claim 1, wherein at least one of the first and second joint actuators is very backdrivable, and thereby has a static backdrive torque less than 5 Nm.

12. The powered prosthesis according to claim 1, wherein at least one of the first and second joint actuators is excessively backdrivable, and thereby has a static backdrive torque less than 2.0 Nm.

13. A powered prosthesis, comprising:
- a first joint actuator, the first joint actuator including a first motor and a first transmission axially aligned with the first motor, wherein the first motor is a first high output torque motor having a peak output torque measured over a 10 second time period of at least about 1.0 Nm;
- a second joint actuator, the second joint actuator including a second motor and a second transmission axially aligned with the second motor, wherein the second motor is a second high output torque motor having a peak output torque measured over a 10 second time period of at least about 1.0 Nm, wherein at least one of the first and second joint actuators is backdrivable, and thereby has a static backdrive torque less than about 10 Nm;
- a connector to connect the first joint actuator with the second joint actuator; and
- a power source connected with both the first and second joint actuator.

14. The powered prosthesis according to claim 13, further including an adapter for connecting the prosthesis with a human body, an inertial measurement unit (IMU) positioned above the first joint actuator, and a controller, the controller including at least a microprocessor.

15. The powered prosthesis according to claim 13, wherein the first joint actuator is a quasi-direct drive actuator having a transmission gear ratio of less than or equal to 24 to 1.

16. The powered prosthesis according to claim 13, wherein the first and second high output torque motors are first and second very high output torque motors having a peak output torque measured over a 10 second time period of at least 1.5 Nm.

17. The powered prosthesis according to claim 13, wherein the first and second high output torque motors are first and second very high output torque motors having a peak output torque measured over a 10 second time period of at least 2.0 Nm.

18. The powered prosthesis according to claim 13, wherein the second joint actuator is a quasi-direct drive actuator having a transmission gear ratio of less than or equal to 24 to 1.

19. The powered prosthesis according to claim 13, wherein at least one of the first transmission and the second transmission has a transmission gear ratio of less than or equal to 22 to 1.

20. The powered prosthesis according to claim 13, wherein both of the first and second joint actuators is backdrivable, and thereby has a static torque less than 10 Nm.

* * * * *